(12) United States Patent
Townley et al.

(10) Patent No.: US 10,286,075 B2
(45) Date of Patent: May 14, 2019

(54) EMBOLIZATION PARTICLE

(71) Applicant: Oxford University Innovation Limited, Oxford (GB)

(72) Inventors: Helen Elizabeth Townley, Oxford (GB); Rachel Anne Bush, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 15/566,254

(22) PCT Filed: Apr. 15, 2016

(86) PCT No.: PCT/GB2016/051059
§ 371 (c)(1),
(2) Date: Oct. 13, 2017

(87) PCT Pub. No.: WO2016/166550
PCT Pub. Date: Oct. 20, 2016

(65) Prior Publication Data
US 2018/0214551 A1    Aug. 2, 2018

(30) Foreign Application Priority Data

Apr. 15, 2015  (GB) .................................. 1506381

(51) Int. Cl.
*A61K 9/00*       (2006.01)
*A61K 41/00*      (2006.01)
(Continued)

(52) U.S. Cl.
CPC ........ *A61K 41/0038* (2013.01); *A61K 9/0019* (2013.01); *A61K 41/0004* (2013.01);
(Continued)

(58) Field of Classification Search
None
See application file for complete search history.

(56) References Cited

U.S. PATENT DOCUMENTS

| | | | |
|---|---|---|---|
| 2006/0257485 A1* | 11/2006 | Kumacheva | B82Y 30/00 424/486 |
| 2009/0053281 A1 | 2/2009 | Richard | |

(Continued)

FOREIGN PATENT DOCUMENTS

| | | |
|---|---|---|
| WO | 2004081072 A2 | 9/2004 |
| WO | 2008045022 A2 | 4/2008 |

(Continued)

OTHER PUBLICATIONS

Danish et al. (2013) Journal of Nanomaterials, 76(4), 332-17.
(Continued)

*Primary Examiner* — Aradhana Sasan
(74) *Attorney, Agent, or Firm* — Dorf & Nelson LLP; Scott D. Locke, Esq.

(57) ABSTRACT

The present invention relates to an embolization particle comprising a microparticle coated with a plurality of nanoparticles, which nanoparticles comprise a metal oxide doped with one or more rare earth elements, wherein the metal oxide is titanium dioxide, zinc oxide or cerium dioxide. An embolization particle of the invention for use in the treatment of cancer in combination with X-ray radiation or proton beam radiation, or use in embolization, is also described. The invention also relates to a process for producing an embolization particle comprising a microparticle coated with a plurality of nanoparticles, which nanoparticles comprise a metal oxide doped with one or more rare earth elements, wherein the metal oxide is titanium dioxide, zinc oxide or cerium dioxide, which process comprises: (i) providing a microparticle; (ii) contacting the microparticle with a plurality of the nanoparticles; and (iii) heating the microparticle and the nanoparticles to form the embolization particle.

18 Claims, 9 Drawing Sheets

Specification includes a Sequence Listing.

(51) Int. Cl.

| | | |
|---|---|---|
| *A61L 24/00* | (2006.01) | |
| *A61L 24/02* | (2006.01) | |
| *A61L 24/06* | (2006.01) | |
| *A61P 31/00* | (2006.01) | |
| *A61P 35/00* | (2006.01) | |
| *A61K 47/69* | (2017.01) | |

(52) U.S. Cl.
CPC ......... *A61L 24/001* (2013.01); *A61L 24/0015* (2013.01); *A61L 24/02* (2013.01); *A61L 24/06* (2013.01); *A61P 31/00* (2018.01); *A61P 35/00* (2018.01); *A61K 47/6923* (2017.08); *A61L 2400/12* (2013.01); *A61L 2420/02* (2013.01); *A61L 2430/36* (2013.01)

(56) References Cited

U.S. PATENT DOCUMENTS

| 2009/0068820 A1 | 3/2009 | Chan et al. |
| 2013/0323306 A1 | 12/2013 | Weber |

FOREIGN PATENT DOCUMENTS

| WO | 2010062267 A1 | 6/2010 | |
| WO | 2011070324 A1 | 6/2011 | |
| WO | WO-2011070324 A1 * | 6/2011 | ............ A61K 33/24 |

OTHER PUBLICATIONS

International Searching Authority, International Search Report, PCT/GB2016/051059, dated Jun. 24, 2016.
International Searching Authority, Written Opinion of the International Searching Authority, PCT/GB2016/051059, dated Jun. 4, 2016.
United Kingdom Intellectual Property Office, IPO Search, GB1506381.1, dated Dec. 7, 2015.
Abramowitz S.D. et al. (2009), Radiology, 250(2) 482-487.
Xu et al. (1998) Supramolecular Science, 5, 449-451.
Morrison et al. (2014) Pharm Res, 31, 2904-2917.
Oh et al. (2011) J. Am. Chem. Soc. 2011, 133(14), 5508-5515.
Horn et al. (2010) Small, 6(11):1185-1190.
Wardman P (2007) Clin. Oncol. (R. Coll. Radiol.), 19, 397-417.
Kaanders et al. (2004) Semin Radiat Oncol, 14, 233-240.
Townley et al. (2012) Nanomedicine, 8, 526-36.
Townley et al. (2012) Nanoscale 4, 5043-50.
Radice et al. (2008) Journal of Colloid and Interface Science, 318(2), 264-270.
Gupta et al. (2011) Chinese Science Bulletin, 56(16), 1639-1657.
Ihara et al. (2009) Materials Chemistry and Physics, 114(1) 1-5.
Uchimura et al. (2011) Materials Chemistry and Physics, 129(3) 871-80.
Kettenbach et al. (2008) Cardiovasc Intervent Radiol, 31(3), 468-476.
Morrison, Rachel et al., Synthesis and characterization of polystyrene embolization particles doped with tantalum oxide nanoparticles for X-ray contrast, J Mater Sci: Mater Med (2015) 26:218.

* cited by examiner

EMBOLIZATION PARTICLE

FIELD OF THE INVENTION

The present invention relates to an embolization particle and compositions comprising a plurality of embolization particles. The use of embolization particles in combination with X-ray radiation or proton beam radiation for the treatment of cancer is also described, as is the use of the particles for embolization. The invention also provides a method for producing an embolization particle.

SEQUENCE LISTING

The computer readable form was submitted in electronic form in a 4 kilobyte file entitled "KEMP_0028_US_CRF.txt" that was created on Oct. 24, 2017.

BACKGROUND OF THE INVENTION

A number of different techniques may be used in the management and treatment of cancers. These include chemotherapeutic methods, radiotherapeutic methods, photodynamic therapy, surgical methods, hormonal therapy and embolization.

Embolization is a non-surgical, minimally invasive procedure in which blood vessels are selectively occluded by introducing emboli. This technique can be used to treat a number of different conditions such as aneurisms, uterine fibroids, and cancer (Abramowitz S. D. et al., Radiology, 2009; 250(2): 482-487). In cancer treatments, embolic particles can be introduced in to the blood stream close to the target and lodge in the small vessels which feed the tumour restricting blood flow. As a result, oxygen and nutrient supplies to the tumour are reduced which causes tumour necrosis.

Radiotherapeutic methods and photodynamic therapy are also effective in reducing tumour size. Photodynamic therapy (PDT) is commonly used to treat some types of cancer. PDT involves injecting a photosensitizing agent into the bloodstream of a patient. The agent is absorbed by cells all over the body, but it generally accumulates in the tumour due to abnormalities or defects in the tumour vasculature. It is also rapidly absorbed by cancer cells, which tend to grow and divide much more quickly than healthy cells and hence have a higher metabolic activity.

Approximately 24 to 72 hours after the injection, when most of the agent has left the normal cells but remains in the tumour, only the tumour is exposed to light of a specific frequency, such as UV light or laser light. The photosensitizing agent that has accumulated in the tumour is excited by exposure to this light and reacts with nearby oxygen or water molecules in the tissue to produce reactive oxygen species (ROS), such as singlet oxygen (average lifetime of 3.7 ms and a diffusion distance of 82 nm), a superoxide radical (average lifetime of 50 ms and a diffusion distance of 320 nm) or a hydroxyl radical (average lifetime of $10^{-7}$ s and a diffusion distance of 4.5 nm). The ROS produced overwhelm the antioxidant defence capacity of nearby cells thereby resulting in the destruction of cancer cells in the tumour.

The short life-times and diffusion distances of the ROS allow cancer cells to be destroyed with little or no damage being caused to neighbouring healthy cells. In addition to directly killing cancer cells, PDT also appears to shrink or destroy tumours by damaging blood vessels in the tumour, thereby depriving it of nutrients. A further benefit is that PDT may also activate the immune system of the patient to attack the tumour cells.

Titanium dioxide is known to generate ROS on exposure to UV light and the effect of titanium dioxide on cultured human adenocarcinoma cells after UV irradiation has been investigated (Xu et al., Supramolecular Science, 5 (1998), 449-451). In this study, transmission electron microscopy (TEM) showed disruption to the cellular membrane and endomembrane system of the cells as a result of oxidative stress. It is believed that the titanium dioxide particles produce hydroxyl radicals that oxidize the membrane lipids of the cells to produce peroxidants, which then set up a series of peroxidant chain reactions. The oxidatively stressed malignant cells progress to a necrotic state that results in their destruction.

Titanium dioxide and many of the photosensitizing agents used in PDT are excited by light of a specific wavelength that cannot penetrate deep into a human body. Consequently, PDT has been limited to the treatment of superficial cancers, such as skin cancers.

Cancers in other locations of the body may instead be treated using radiotherapy, which involves the use of ionizing radiation, such as X rays or proton beam radiation. However, some types of cancer, such as renal cell cancer, are radioresistant because the doses of radiation required to destroy the cancer are too high to be safe in clinical practice. Higher doses of radiation are also associated with an increased risk of causing cancer.

WO 2011/070324 describes metal oxide nanoparticles doped with rare earth elements. These particles have been shown to be effective in the causing cell death on exposure to X-ray radiation.

Morrison et al., Pharm Res (2014) 31:2904-2917 describes microparticles coated with nanoparticles comprising chemotherapeutic agents.

It is an object of the present invention to provide a new form of treatment for cancers.

SUMMARY OF THE INVENTION

The inventors have found that multimodal embolization particles that combine embolization efficacy with radiotherapeutic efficacy may be produced. This offers a new technique for treating cancer by simultaneously embolizing tumour vasculature and radiotherapeutically treating the tumour. It has also surprisingly been found that the embolization particle of the invention comprises nanoparticles which are radiotherapeutically effective even under hypoxic conditions.

Thus, the invention provides an embolization particle comprising a microparticle coated with a plurality of nanoparticles, which nanoparticles comprise a metal oxide doped with one or more rare earth elements, wherein the metal oxide is titanium dioxide, zinc oxide or cerium dioxide.

The invention further provides a composition comprising a plurality of embolization particles, wherein each embolization particle comprises a microparticle coated with a plurality of nanoparticles, which nanoparticles comprise a metal oxide doped with one or more rare earth elements, wherein the metal oxide is titanium dioxide, zinc oxide or cerium dioxide.

Also provided by the invention is a pharmaceutical composition comprising a plurality of embolization particles as defined herein and one or more pharmaceutically acceptable excipients or diluents.

The invention also provides an embolization particle of the invention, a composition of the invention or a pharmaceutical composition of the invention, for use in the treatment of cancer in combination with X-ray radiation or proton beam radiation. Further provided is an embolization particle, composition or pharmaceutical composition of the invention, for use in embolization.

The invention further provides a method of treating cancer in a subject comprising:

a) administering to a subject an embolization particle, a composition, or a pharmaceutical composition of the invention; and b) directing X-ray radiation, or proton beam radiation, at a locus or site of the cancer or tumour tissue.

The invention further provides a process for producing an embolization particle comprising a microparticle coated with a plurality of nanoparticles, which nanoparticles comprise a metal oxide doped with one or more rare earth elements, wherein the metal oxide is titanium dioxide, zinc oxide or cerium dioxide, which process comprises: (i) providing a microparticle; (ii) contacting the microparticle with a plurality of the nanoparticles; and (iii) heating the microparticle and the nanoparticles to form the embolization particle.

DETAILED DESCRIPTION OF THE INVENTION

Figure 1:
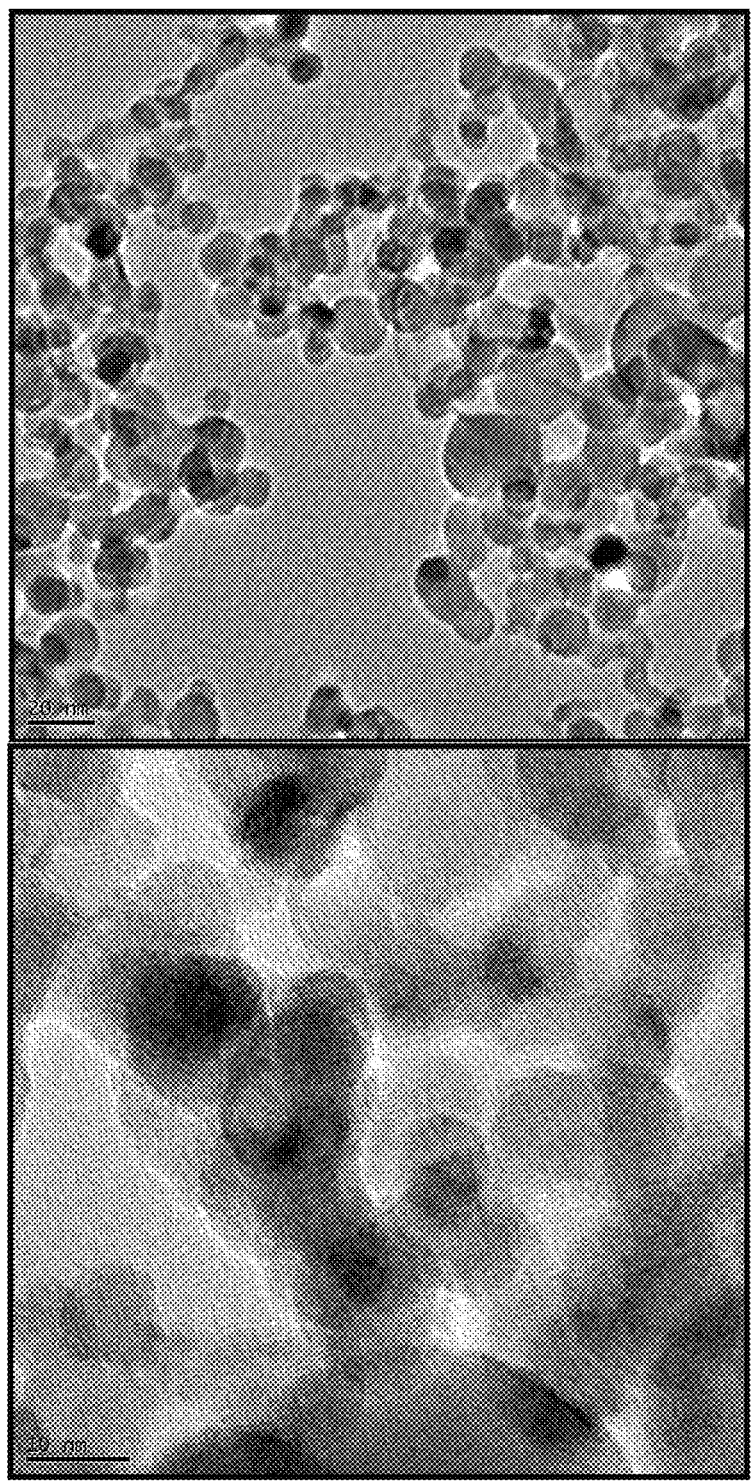
FIG. 1 shows transmission electron micrographs (TEMs) of Gd doped $TiO_2$ ($TiO_2$:Gd) nanoparticles showing size, shape and crystallinity at two scales.

The invention provides an embolization particle comprising a microparticle coated with a plurality of nanoparticles, which nanoparticles comprise a metal oxide doped with one or more rare earth elements, wherein the metal oxide is titanium dioxide, zinc oxide or cerium dioxide. The invention also provides a plurality of nanoparticles according to the invention.

The microparticle is coated with the plurality of nanoparticles. It is the surface of the microparticle which is usually coated with the nanoparticles. Thus, the microparticle typically forms the core of the embolization particle and the nanoparticles typically form a coating, or outer layer, on the core. The coating of the nanoparticles is typically continuous, i.e. substantially the entire surface (e.g. greater than 95% of the surface) of the microparticle is coated with the nanoparticles. The coating of nanoparticles usually comprises several layers of nanoparticles and may have a thickness of over 30 nm. The coating does not necessarily require that any additional material is required to fix (coat) the nanoparticles to the surface and the nanoparticles typically adhere directly to the surface of the microparticle. As discussed below, the nanoparticles may be sintered with the microparticle and this typically causes the nanoparticles to coat the microparticle.

Typically the core of the embolization particle comprises the microparticle and the outermost layer of the embolization particle comprises the nanoparticles. In some cases, the core of the embolization particle may consist of the microparticle and the outermost layer of the embolization particle may consist of the nanoparticles. The microparticle may additionally comprise some of the nanoparticles, or other different nanoparticles.

The embolization particle may have a diameter of from 1 to 500 μm, for instance from 1 to 100 μm. Typically, the size of the embolization particle is from 5 to 100 μm or from 5 to 50 μm. The size distribution for a plurality of embolization particles may be matched to the vasculature of a tumour as discussed further below.

As used herein, the term "diameter" in the context of a diameter of a single particle refers to the diameter of a sphere having the same volume as the particle. Thus, if the particle is spherical, the diameter or the particle is simply the diameter. If the particle is not spherical (for instance spheroidal), then the diameter of the particle is the diameter of a spherical particle having the same volume.

The embolization particle typically has a high sphericity. Thus, the particles are typically rounded particles. The sphericity of the embolization particle is typically from 0.8 to 1.0. The sphericity may be calculated as $$\pi^{\frac{1}{3}}(6V_p)^{\frac{2}{3}}/A_p$$

where $V_p$ is the volume of the particle and $A_p$ is the area of the particle. Perfectly spherical particles have a sphericity of 1.0. All other particles have a sphericity of lower than 1.0. The average sphericity of a plurality of the embolization particles is typically from 0.8 to 1.0. The particles may alternatively be non-spherical, for instance in the form of oblate or prolate spheroids. The embolization particle typically has a smooth surface.

Nanoparticles

The metal oxide may be titanium dioxide, zinc oxide or cerium dioxide. The metal oxide is typically titanium dioxide (also referred to as titania). Thus, the metal oxide is typically $TiO_2$ which may be in any amorphous or crystalline form. The $TiO_2$ may be anatase or rutile titania. The nanoparticles may comprise zinc oxide (ZnO) or cerium oxide ($CeO_2$; also known as ceria). Each nanoparticle may comprise one or more of titanium dioxide, zinc oxide or cerium dioxide. Some nanoparticles in the embolization particle may comprise one or more of titanium dioxide, zinc oxide or cerium dioxide and other nanoparticles in the embolization particle may comprise a different combination of one or more of titanium dioxide, zinc oxide or cerium dioxide.

The one or more rare earth elements may be any suitable rare earth elements selected from the Period Table of the Elements. The rare earth elements include the lanthanide elements together with scandium and yttrium. Thus, the one or more rare earth elements are typically selected from Sc, Y, La, Ce, Pr, Nd, Pm, Sm, Eu, Gd, Tb, Dy, Ho, Er, Tm and Yb. The nanoparticles may be doped with two or more rare earth elements or three or more rare earth elements.

The one or more rare earth elements may be selected from the lanthanides, i.e. La, Ce, Pr, Nd, Pm, Sm, Eu, Gd, Tb, Dy, Ho, Er, Tm, and Yb or La, Ce, Pr, Nd, Sm, Eu, Gd, Tb, Dy, Ho, Er, Tm, and Yb (excluding Pm due to its radioactivity, although such radioactivity may in some applications be desired). The one or more rare earth elements may be one or more, two or more, or three or more, elements selected from La, Ce, Pr, Nd, Pm, Sm, Eu, Gd, Tb, Dy, Ho, Er, Tm, Yb. The one or more rare earth elements are preferably selected from Gd, Eu, Er and Nd. The one or more rare earth elements may include Gd. The one or more rare earth elements may include Eu. The one or more rare earth elements may include Er. The one or more rare earth elements may include Nd. Preferably, the one or more rare earth elements include Gd. The metal oxide may be doped with a single rare earth element, for instance Gd. The metal oxide may be doped with two or more of the rare earth elements.

The rare earth element is generally present as a dopant in the host lattice of the metal oxide in the form of a cation. When the metal oxide is cerium oxide, then the cerium oxide is preferably doped with at least one rare earth element other than cerium. The nanoparticle may consist essentially of the metal oxide and the rare earth element, for instance comprising greater than or equal to 98 wt % of the metal oxide and the rare earth element.

The presence of one or more rare earth elements as a dopant in the host lattice of titanium dioxide, zinc oxide or cerium oxide allows these metal oxides to be excited by X-rays, or other ionising radiation such as proton beam radiation, to generate free radicals, such as reactive oxygen species (ROS), which have use in the treatment of a human or animal body. The amount of ROS generated by the doped metal oxide will depend on, amongst other things, the identity of the rare earth element dopant and the energy of the X-rays used as part of the treatment. Thus, the metal oxide and the rare earth element(s) can be selected to generate a suitable amount of ROS when X-rays of a specific wavelength (i.e. energy) are used as part of the treatment. This may be achieved by selecting a rare earth element as a dopant that strongly absorbs X-rays at an energy that falls within the energy range of the incident X-rays.

In practice, apparatus that is conventionally used to generate X-rays for medical use, whether for radiotherapy or for diagnostic imaging (e.g. radiography), tends to produce X-rays having energies in certain ranges. Normally, the energy of the X-rays used in radiotherapy tends to be higher than that of those used for diagnostic imaging. For instance, X-rays used in radiotherapy may have an energy of greater than or equal to 0.04 MeV or as further discussed hereinbelow.

Typically, the metal oxide is doped with gadolinium (Gd). Preferably, the metal oxide is doped with gadolinium and one or more of europium (Eu), erbium (Er) or neodymium (Nd). Thus, the metal oxide may preferably be doped with Gd and Eu; Gd and Er; Gd and Nd; Gd, Eu and Er; Gd, Eu and Nd; Gd, Er and Nd; or Gd, Eu, Er and Nd. The metal oxide may be doped with gadolinium, europium and erbium.

The metal oxide may in some cases be doped with europium. Preferably, the metal oxide is doped with europium and one or more of gadolinium, erbium or neodymium. Thus, the metal oxide may preferably be doped with Eu and Er; Eu and Nd; or Eu, Er and Nd.

The metal oxide may, for instance, be doped with erbium. Preferably, the metal oxide is doped with erbium and one or more of gadolinium, europium or neodymium. Thus, the metal oxide may preferably be doped with Er and Eu; or Er and Nd.

The metal oxide may, for example, be doped with neodymium. Preferably, the metal oxide is doped with neodymium and one or more of gadolinium, europium or erbium. Often the metal oxide is titanium and the one or more dopant elements comprise gadolinium.

In general, the metal oxide is doped with one or more rare earth elements in a total amount of from 0.1 to 25 mol % (e.g. 7.5 to 25 mol %), preferably 1 to 20 mol %, more preferably 2.5 to 15 mol %, especially 5 to 13.5 mol %, and even more preferred is 7.5 to 12.5 mol %. Typically, the metal oxide is doped with the one or more rare earth elements in a total amount of from 0.1 to 25 mol % relative to the amount of metal oxide.

The metal oxide may be doped with gadolinium and at least one other rare earth metal, wherein the metal oxide is doped with gadolinium in an amount of 1 to 12.5 mol %, preferably from 5 to 10 mol %.

The metal oxide may be doped with (i) gadolinium in an amount of from 3.5 to 12.5% by weight; (ii) europium in an amount of from 0.5 to 1.5% by weight; and (iii) erbium in an amount of from 0.5 to 1.5% by weight. For instance, the metal oxide may be doped with (i) gadolinium in an amount of from 5 to 10% by weight; (ii) europium in an amount of from 0.75 to 1.25% by weight (e.g. about 1% by weight); and (iii) erbium in an amount of from 0.75 to 1.25% by weight (e.g. about 1% by weight).

The metal oxide may, for example, be doped with (i) gadolinium in an amount of from 3.5 to 12.5 mol %; (ii) europium in an amount of from 0.5 to 1.5 mol %; and (iii) erbium in an amount of from 0.5 to 1.5 mol %. More preferably, the metal oxide is doped with (i) gadolinium in an amount of from 5 to 10 mol %; (ii) europium in an amount of from 0.75 to 1.25 mol % (e.g. about 1 mol %); and (iii) erbium in an amount of from 0.75 to 1.25 mol % (e.g. about 1 mol %).

The total amount of one or more rare earth elements incorporated as a dopant or dopants in the metal oxide will depend on the relative molar amount of the rare earth element containing starting material to the starting material used to prepare the metal oxide. The amount of rare earth element incorporated as a dopant in the metal oxide may depend on the method used to manufacture the particles, which method may be routinely be adapted to obtain the desired amount of dopant in the particles. The amount of rare earth element as a dopant in the metal oxide(s) can readily be measured using techniques that are well known to a person skilled in the art. The amount of rare earth elements may for instance be measured by energy-dispersive X-ray spectroscopy (EDX). When a plurality of particles of the invention are present or are used as part of a therapy or treatment, the amounts above in mol % refer to the average (i.e. mean) total amount of the rare earth element(s) that dope the metal oxide(s) of the particles.

The nanoparticles used typically have an average diameter of less than 200 nm. The average diameter of the particles is typically measured from transmission electron micrograph (TEM) images. The average diameter may be the median mass diameter (MMD). The MMD is the diameter for which half of the particles by mass are larger (i.e. have a diameter larger than the MMD) and half are smaller (i.e. have a diameter smaller than the MMD). MMD may be measured by a number of known techniques. The mass median diameter is a well recognised measure of particle size distribution.

Often, the nanoparticles used have an average diameter of less than 100 nm. It is preferred that the nanoparticles have an average diameter of from 1 to 100 nm. More preferably the nanoparticles have an average diameter of from 5 to 75 nm (e.g. 10 to 75 nm), particularly from 10 nm to 65 nm.

The nanoparticles useful in the embolization particle of the invention may be as further described in WO 2011/070324, the entirety of which is incorporated herein by reference.

The nanoparticles used in the embolization particle may be synthesised by any suitable method, for instance those described in WO 2011/070324. A general methodology may be as follows.

One or more rare earth element compounds (e.g. metal salts) are combined with a first solvent and a metal oxide precursor (e.g. a metal alkoxide). The amount of rare earth element compound that is combined with the solution determines the amount of dopant that is introduced into the host lattice of the metal oxide. A total amount of up to 25 mol % of one or more rare earth elements may be introduced into the host lattice of the metal oxide. As an example, 1 millimoles of a rare earth element salt were added to 100 millimoles of metal oxide precursor to produce metal oxide particles doped with 1 mol % rare earth element.

The solution may then be added drop wise to a second solvent, optionally whilst stirring vigorously. The mixture may be stirred for a further time (for instance from 1 to 15 minutes) and the precipitate then allowed to settle. The supernatant may then be removed and the precipitate washed with a third solvent and stirred for a further time (for instance from 1 to 20 mins). The supernatant is typically subsequently collected by filtration and optionally then autoclaved in tubes half-filled with ddH$_2$O. The resulting slurry is typically then dried and the samples optionally ground. The resulting nanoparticles may be subsequently fired for instance at a temperature of from 300° C. to 1000° C. for a time of from 1 to 10 hours.

The rare earth element compound is typically a salt of the rare earth element. Thus, the rare earth element compound is typically a halide, nitrate, sulfate or acetate salt of the rare earth element. Preferably, the rare earth element compound is a nitrate salt of the rare earth element. The rare earth element compound which is a salt may be in the form of a hydrate. For instance, the one or more rare earth element salts may be selected from gadolinium (III) nitrate hexahydrate, europium (III) nitrate hydrate, terbium (III) nitrate pentahydrate, neodymium nitrate hexahydrate and erbium (III) nitrate pentahydrate.

The metal oxide precursor may be any suitable precursor for the metal oxide compound, i.e. any compound which converts to the metal oxide under appropriate conditions, typically under hydrolysis. The metal oxide precursor is often an organometallic compound comprising the metal or a salt of the metal. For instance, the metal oxide precursor may be a metal alkoxide or a metal nitrate. The precursor for titania is typically a titanium alkoxide, for instance titanium (IV) isopropoxide or titanium (IV) ethoxide, preferably titanium (IV) isopropoxide. The precursor for ceria is typically cerium nitrate. The precursor for zinc oxide is typically zinc nitrate.

The first, second and third solvents may be any suitable solvents. Each solvent may be a polar solvent or a non-polar solvent. Typically the first, second or third solvent is a polar solvent. Examples of polar solvents include water, alcohol solvents (such as methanol, ethanol, n-propanol, isopropanol and n-butanol), ether solvents (such as dimethylether, diethylether and tetrahydrofuran), ester solvents (such as ethyl acetate), carboxylic acid solvents (such as formic acid and ethanoic acid), ketone solvents (such as acetone), amide solvents (such as dimethylformamide and diethylformamide), amine solvents (such as triethylamine), nitrile solvents (such as acetonitrile), sulfoxide solvents (dimethylsulfoxide) and halogenated solvents (such as dichloromethane, chloroform, and chlorobenzene). The first, second, or third solvent may be selected from polar protic solvents. Examples of protic polar solvents include water, methanol, ethanol, n-propanol, isopropanol, n-butanol, formic acid, ethanoic acid. Examples of non-polar solvents include alkanes (such as pentane and hexane), cycloalkanes (such as cyclopentane and cyclohexane), and arenes (such as benzene, toluene and xylene). Preferably the solvent is a polar solvent. More preferably, the solvent is a polar aprotic solvent. Examples of polar aprotic solvents include ketone solvents (such as acetone), amide solvents (such as dimethylformamide and diethylformamide), nitrile solvents (such as acetonitrile), sulfoxide solvents (dimethylsulfoxide) and halogenated solvents (such as dichloromethane, chloroform, and chlorobenzene).

Typically, the first, second or third solvent comprises a polar protic solvent such as an alcohol. The first solvent typically comprises very little water, for instance less than 5% (or less than 1%) by volume. Thus, the first solvent may be anhydrous. The first solvent may be selected from methanol, ethanol, propanol, isopropanol and butanol, for instance selected from dry methanol, dry ethanol, dry propanol, dry isopropanol and dry butanol.

The second solvent typically comprises water. The second solvent may further comprise an alcohol, for instance methanol, ethanol, propanol, isopropanol and butanol, preferably isopropanol. The second solvent may therefore be a water/isopropanol mix, for instance in a volume/volume ratio (v/v) of from 10/90 to 90/10 or 40/60 to 60/40. The water/isopropanol mix is typically about 50/50 v/v.

The third solvent may be any solvent suitable for washing the nanoparticles, for instance an ether or an alcohol such as isopropanol.

For instance, the method may be as follows: one or more rare earth metal compounds selected from gadolinium (III) nitrate hexahydrate, europium (III) nitrate hydrate, terbium (III) nitrate pentahydrate, neodymium nitrate hexahydrate, and erbium (III) nitrate pentahydrate may be suspended in from 1 to 100 mL of titanium (IV) isopropoxide and then 10 to 100 mL dry isopropanol may be added.

The amount of rare earth metal compound that is suspended in the solution determines the amount of dopant that is introduced into the host lattice of titanium dioxide. A total amount of up to 25 mol % of one or more rare earth elements may be introduced into the host lattice of the titanium dioxide. As an example, 1 millimoles of gadolinium nitrate were added to 100 millimoles of titanium isopropoxide to produce titanium dioxide particles doped with 1 mol % gadolinium.

The solution may then be added drop wise to a 50/50 (v/v) water/isopropanol mix whilst stirring vigorously. The mixture may be stirred for a further time (e.g. 5 minutes) and the precipitate allowed to settle. The supernatant may be removed and the precipitate washed with isopropanol and stirred for a further time (e.g. 10 minutes). The supernatant may be subsequently collected by filtration and then autoclaved in tubes half-filled with $ddH_2O$. The slurry may be then kept at 100° C. until dry. Samples are typically ground to a fine powder and subsequently fired at various temperatures (e.g. 3 hours at 700° C.).

The nanoparticles may alternatively be produced by flame spray pyrolysis (FSP). FSP is a promising technique for fast and scalable synthesis of nanoparticles. Precursors are dissolved/dispersed in a highly exothermic solvent and combusted in a flame. The mechanism of particle formation is based on a gas-to-matter principle and can be divided into four main steps: (i) precursor spray evaporation/decomposition forming metal vapour, (ii) nucleation as a result of supersaturation, (iii) growth by coalescence and sintering, and (iv) particle aggregation/agglomeration.

Producing the nanoparticles by flame spray pyrolysis typically comprises (i) spraying a composition comprising a solvent and one or more precursor compounds (optionally through an outlet or a nozzle) to produce a plurality of droplets and (ii) combusting the droplets of the composition to form the nanoparticles. The solvent is typically a highly exothermic solvent, for instance a flammable organic solvent. For instance, the solvent may comprise methanol or ethanol. The one or more precursor compounds typically comprise oxides, alkoxides or carboxylates of the metals to form the nanoparticles. For instance, the one or more precursor compounds may comprise titanium (IV) isopropoxide and one or more rare earth compounds selected from gadolinium (III) nitrate hexahydrate, europium (III) nitrate hydrate, terbium (III) nitrate pentahydrate, neodymium nitrate hexahydrate, and erbium (III) nitrate pentahydrate. The nanoparticles produced by FSP may be collected by filtration. After production by FSP, the nanoparticles may be fired by heating to a temperature of from 300° C. to 800° C. for from 0.1 to 5 hours.

Microparticle

The embolization particle comprises a microparticle on which the nanoparticles are coated. The microparticle may be any microparticle which is suitable for use in an embolization particle. The microparticle is usually a microparticle which would also be suitable for use alone as an embolization particle.

Typically, the microparticle has a diameter of from 0.1 to 500 µm, for instance from 1 to 500 µm. Preferably, the microparticle has a diameter of from 10 to 200 µm. For instance, the microparticle may have a diameter of from 10 to 100 µm, for instance from 20 to 90 µm, from 10 to 80 µm, from 20 to 60 µm, or from 30 to 50 µm. Often, the microparticle has a diameter of from 10 to 60 µm.

The material from which the microparticle is made is typically an inert material, for instance a material which is unlikely to react on exposure to ambient conditions or moisture. The microparticle is often biologically inert. The microparticle typically comprises one or more materials selected from a polymer, a metal and an inorganic compound. The microparticle often comprises greater than 80 wt %, greater than 90 wt % or greater than 95 wt %, of a material selected from a polymer, a metal and an inorganic compound. Preferably, the microparticle comprises a polymer. The microparticle may comprise greater than 80 wt %, greater than 90 wt % or greater than 95 wt %, of a polymer. The microparticle may consist essentially of a polymer (e.g. greater than 99 wt %).

Examples of suitable polymers include polyalkenes, polyalkynes, polyethers, polyamides, polyesters, and polyacrylates. Each of these may be polymers (i.e. comprising a single type of monomer) or copolymers (i.e. comprising two or more different types of monomers). A copolymer comprising two or more monomer units, at least one of which monomer units is derived from an alkene, may be referred to as a polyalkene. Examples of polyalkenes include polyethene, polypropene, polystyrene, styrene divinylbenzene copolymer, polyvinyl chloride, polyvinyl alcohol, polymethylpentene, polybut-1-ene, polyisobutylene, ethylene propylene rubber, ethylene propylene diene monomer rubber. Examples of polyalkynes include polyethyne and polypropyne. Examples of polyethers include polyethylene glycol and polyphenyl ether. Examples of polyamides include polyamide 4, polyamide 6, polyamide 44 and polyamide 66. Examples of polyesters include polyethylene terephthalate and polybutylene terephthalate. Examples of polyacrylates include poly(methyl methacrylate) and poly(methyl acrylate).

The microparticle may comprise a metal, typically a metal which is inert to oxidation under ambient conditions. For instance, the metal may be selected from metals such as Fe, Cu, Zn, Ni, Co, Cr, Mn, Ag, Au, Al, Pt, Pd, Rh and V.

The microparticle may comprise an inorganic compound, which inorganic compound is typically insoluble. The inorganic compound may for instance be silica or alumina.

Preferably, the microparticle comprises a polymer or copolymer. The microparticle may comprise greater than 90 wt % or greater than 95 wt % of a polymer or copolymer. Typically, the microparticle comprises one or more polymers or copolymers selected from polyalkenes, polyacrylates, polyesters and polyether. The polymer or copolymer is preferably cross-linked.

Preferably, the microparticle comprises a polymer or copolymer formed from styrene monomer units. The microparticle may comprise polystyrene or copolymer of styrene and another monomer, for instance a diacrylate or divinylbenzene. For example, the microparticle may comprise a copolymer of styrene and a diacrylate, which diacrylate may be selected from ethylene glycol dimethacrylate, ethylene glycol diacrylate, propylene glycol dimethacrylate, propylene glycol diacrylate, poly(ethylene glycol) dimethacrylate, poly(ethylene glycol) diacrylate, poly(propylene glycol) dimethacrylate, poly(propylene glycol) diacrylate, hexane-1,6-diol diacrylate and hexane-1,6-diol dimethacrylate. Preferably, the microparticle comprises a copolymer of styrene and ethylene glycol dimethacrylate, or a polymer which is polystyrene. The molecular weight of the polymer or copolymer may be any suitable value.

The polymer used in the microparticle may be obtainable by suspension copolymerisation of styrene and ethylene glycol dimethacrylate (EGDMA). For example an oil phase may be created by mixing styrene and EGDMA with an initiator such as azobisisobutyronitrile (AIBN; Aldrich). The oil phase may then be added to aqueous polyvinyl alcohol.

The thickness of the coating of nanoparticles is typically from 10 to 300 nm. For instance, the thickness of the coating of nanoparticles is may be from 10 to 100 nm or from 20 nm to 80 nm. The embolization particle may comprise from 0.1 to 50 wt % of nanoparticles, for instance from 1 to 10 wt %.

Additional Modality of Embolization Particles

Further features may be introduced into the embolization particles of the invention, thus producing multimodal embolization particles. For instance, the embolization particles can also incorporate imaging agents such as fluorophores or heavy metals such as tantalum as X-ray contrast agents (non-magnetic so allows patient to undergo MRI), or be combined with chemoembolization (a mixture of mesoporous silica nanoparticles and titania nanoparticles).

For instance, the embolization particle may further comprise a plurality of radioopaque nanoparticles. Typically, the radioopaque particles are radioopaque with respect to X-rays. The radioopaque nanoparticles may be form part of the coating on the embolization particle or they may form part of the microparticle. Typically, the radioopaque nanoparticles are incorporated into the microparticle. Thus, the radioopaque nanoparticles may form part of the core of the embolization particle, for instance by being incorporated into the structure of the microparticle. The radioopaque nanoparticles are typically incorporated into the microparticle by adding the radioopaque nanoparticles to the reaction mixture from which the microparticle is produced.

The radioopaque nanoparticles typically comprise tantalum oxide, gold or bismuth (III) sulfide. Preferably the radioopaque nanoparticles comprise tantalum oxide. The radioopaque particles may have an average diameter of from 10 to 100 nm.

The radioopaque nanoparticles comprising tantalum oxide may be produced by the method as described in Oh et al, J Am Chem Soc 2011;133(14):5508-5515. Typically, the tantalum oxide nanoparticles are produced by hydrolysing tantalum (V) ethoxide.

The embolization particle may additionally comprise from 0.1 to 10 wt % of the radioopaque nanoparticles.

The embolization particle may additionally or alternatively further comprise a chemotherapeutic agent. The chemotherapeutic agent may be any suitable chemotherapeutic agent. For instance, the chemotherapeutic agent may be one or more agents selected from alkylating agents, antimetabolites, anti-microtubule agents, topoisomerase inhibitors and cytotoxic antibiotics. The chemotherapeutic agent may be selected from ophiobolin A, ophiobolin C, vinca alkaloids, taxanes, dihydrofolate reductase inhibitors, thymidylate synthase inhibitors, adenosine deaminase inhibitors, thiopurines, DNA polymerase inhibitors, hypomethylating agents, campototheca, nitrogen mustards, nitrosoureas, carboplatin, cisplatin and nedaplatin.

The chemotherapeutic agent is typically incorporated into nanoparticles in the embolization particle. The embolization particle may therefore further comprise a plurality of nanoparticles which comprise the chemotherapeutic agent.

The nanoparticles which comprise the chemotherapeutic agent are typically coated onto the surface of the microparticle. Thus the coating on the microparticle may comprise a mixture of the rare earth doped metal oxide nanoparticles described above and nanoparticles comprising a chemotherapeutic agent.

The nanoparticles which comprise the chemotherapeutic agent are typically silica nanoparticles. The nanoparticles which comprise the chemotherapeutic agent may have an average diameter of from 10 to 100 nm. The silica nanoparticles may be produced by hydrolysing tetraethyl orthosilicate (for instance as described in Hom et al, Small. 2010; 6(11):1185-90). The nanoparticles comprising a chemotherapeutic agent may be as described in Morrison et al., Pharm Res (2014) 31:2904-2917.

The embolization particle may additionally comprise from 0.1 to 10 wt % of the chemotherapeutic agent.

The nanoparticles used in the invention may additionally comprise at least one targeting moiety. Typically, the targeting moiety is a peptide, a polypeptide, a nucleic acid, a nucleotide, a lipid, a metabolite, an antibody, a receptor ligand, a ligand receptor, a hormone, a sugar, an enzyme, a vitamin or the like. For example, the targeting moiety may be selected from a drug (e.g. trastuzumab, gefitinib, PSMA, tamoxifen/toremifen, imatinib, gemtuzumab, rituximab, alemtuzumab, cetximab), a DNA topoisomerase inhibitor, an antimetabolite, a disease cell cycle targeting compound, a gene expression marker, an angiogenesis targeting ligand, a tumour marker, a folate receptor targeting ligand, an apoptotic cell targeting ligand, a hypoxia targeting ligand, a DNA intercalator, a disease receptor targeting ligand, a receptor marker, a peptide (e.g. a signal peptide, a melanocyte stimulating hormone (MSH) peptide), a nucleotide, an antibody (e.g. an antihuman epidermal growth factor receptor 2 (HER2) antibody, a monoclonal antibody C225, a monoclonal antibody CD3 1, a monoclonal antibody CD40), an antisense molecule, an siRNA, a glutamate pentapeptide, an agent that mimics glucose, amifostine, angiostatin, capecitabine, deoxycytidine, fullerene, herceptin, human serum albumin, lactose, quinazoline, thalidomide, transferrin and trimethyl lysine. Preferably, the targeting moiety is a nuclear localization signal (NLS) peptide. An example of an NLS peptide is PPKKKRKV (SEQ ID NO: 1) or CGGFSTSLRARKA (SEQ ID NO: 2). Preferably, the NLS peptide is CGGFSTSLRARKA (SEQ ID NO: 2).

Composition

The invention also provides a composition comprising a plurality of embolization particles, wherein each embolization particle comprises a microparticle coated with a plurality of nanoparticles, which nanoparticles comprise a metal oxide doped with one or more rare earth elements, wherein the metal oxide is titanium dioxide, zinc oxide or cerium dioxide. The embolization particles may as further defined hereinbefore.

The particle size distribution of the embolization particles in the composition may be any suitable distribution. Typically, the embolization particles have an average diameter of from 10 to 200 µm.

The particle size distribution of the embolization particles of the invention may be varied to correspond closely with the distributions of vascular diameter found in various tumours and therefore more effectively occlude vasculature within the tumour. This allows effective embolization of the desired vasculature. In one embodiment, the plurality of embolization particles according to the invention have an average diameter similar in value to (e.g. a value between 90 and 100% of) the mean diameter of the vasculature in the tumour to be treated. For instance, the average diameter of the embolization particles may be from 15 to 200 µm, from 10 to 100 µm, or from 20 to 50 µm.

Examples of the diameter of vasculature in various tumours are given in Table 1 below.

TABLE 1

| Human or animal | Tumour type | Study size | Diameter of vasculature measured | Size distribution of vessels measured |
|---|---|---|---|---|
| Human | Prostate | 572 patients | Mean = 25.2 µm Range = 12.9-55.6 µm | Not reported |
| Human | Prostate | 62 patients | Mean = 24.4 µm | Not reported |

TABLE 1-continued

| Human or animal | Tumour type | Study size | Diameter of vasculature measured | Size distribution of vessels measured |
|---|---|---|---|---|
| Human | Laryngeal | 16 patients | Range = 5->60 μm | 75% were 5-20 μm 1% was >60 μm |
| Mouse | Colorectal | 15 tumours | Range = 2-55 μm | 75% were <80 μm |
| Mouse | Colon | 1500 vessels | Range = 4-29 μm | Not reported |
| Mouse | Mammary carcinomas | 6 tumours | Mean = 39 μm Range = 0-225 μm | Majority of the vessels were 0-50 μm |
| Mouse | Human cervical epithelial adenocarcinoma | 25 vessels | Range = 5-60 μm | Not reported |
| Rat | Mammary adenocarcinoma | 4 tumours | Range = 5-225 μm | Majority of the vessels were small |
| Rat | Colon | 22 tumours | Range = 5-100 μm | Majority of the vessels were 5-50 μm |
| Rat | Glioma | 3138 vessels measured | Mean = 16.8 μm Range = 1-50 μm | Peak vessel size was 10 μm |

Pharmaceutical Compositions and Use

The present invention also provides a pharmaceutical composition comprising a plurality of embolization particles as defined herein and one or more pharmaceutically acceptable excipients or diluents. The embolization particles of the invention are typically administered parenterally, whether subcutaneously, intravenously, intramuscularly, intrasternally, transdermally or by infusion techniques. Thus, the pharmaceutical composition is typically suitable for parenteral administration. Preferably, the pharmaceutical composition is suitable for intravenous parenteral administration.

Suspensions and emulsions may contain as an excipient, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable diluent, e.g. sterile water, olive oil, ethyl oleate, glycols, e.g. propylene glycol, and if desired, a suitable amount of lidocaine hydrochloride.

Solutions for injection or infusion may contain as diluent, for example, sterile water or preferably they may be in the form of sterile, aqueous, isotonic saline solutions.

Typically, the concentration of the embolization particles in the pharmaceutical composition is from 100 particles/ml to $10^{10}$ particles/ml, for example from $10^4$ particles/ml to $10^8$ particles/ml. Often, the total number of embolization particles in the composition may be from 10 to $10^6$, or from 20 to 10000.

In general, the pharmaceutical composition will comprise a therapeutically effective amount of the particles of the invention. It will be appreciated by one of skill in the art that appropriate dosages of the particles and a pharmaceutical composition comprising the particles can vary from patient to patient. Determining the optimal dosage will generally involve balancing of the level of therapeutic benefit through embolization and release of ROSs against any risk or deleterious side effects. The selected dosage level will depend on a variety of factors including the route of administration, the time of administration, the rate of excretion of the particles, the duration of the treatment, other compounds and/or materials used in combination, the severity of the condition, and the species, sex, age, weight, condition, general health, and prior medical history of the patient. The amount of particles and route of administration will ultimately be at the discretion of the physician, veterinarian, or clinician, although generally the dosage will be selected to achieve local concentrations at the site of action that achieve the desired effect.

The invention also provides an embolization particle as defined herein for use in the treatment of cancer in combination with X-ray radiation or proton beam radiation. Typically, the treatment is in combination with X-ray radiation. The cancer is typically cancer of the lung, liver, kidney, bladder, breast, head and neck, brain, ovaries, prostate, intestine, colon, rectum, uterus, pancreas, eye, bone marrow, lymphatic system or thyroid gland.

The embolization particle of the invention contains nanoparticles which have been found to be radiotherapeutically effective under hypoxic conditions. The efficacy of conventional radiotherapy relies upon an adequate supply of oxygen to the tumour cells; however, it is now well-established that human solid tumours contain a substantial fraction of cells which are hypoxic. This chronic hypoxia which is seen in tumours is often referred to as diffusion-limited hypoxia since it arises from the large intervascular distance which is beyond the diffusion limit of oxygen (estimated to be between 75 and 200 μm). Additionally transient 'acute' perfusion-limited hypoxia may occur because of unstable blood flow in vessels, which results in periods of time when blood flow to a region is decreased or blocked. When tissue becomes hypoxic several signalling pathways are activated, altering the behaviour of the cells to enable them to adapt to oxygen deprivation. These include an increase in the capacity for anaerobic glycolysis for energy production and in vivo mediate changes in blood flow and stimulate angiogenesis. However in the context of radiotherapy, the concentration of oxygen during, or within milliseconds of irradiation is critical in determining DNA damage and subsequent biological response, with the biological effectiveness of a given dose significantly greater for well-oxygenated cells compared to hypoxic cells. For X-rays oxygen enhancement ratio (OER, defined as the ratio of doses under hypoxia compare to aerated conditions required to produce the same biological effect) values of between 2.5 and 3.5 are typically reported for a range of biological endpoints including clonogenic survival. Enhancement of the efficacy of radiotherapy using radiosensitizers which can act under hypoxic (and also normoxic conditions) would be a promising way to achieve improved therapeutic outcome. A number of radiosensitizers for hypoxic cells have been described in the literature. These are primarily the nitroimidazoles which are found to mimic the effect of oxygen in the radiochemical process (Adams GE: Cancer (ed 6). New York, N.Y., F. F. Becker Plenum Press, 1977; Wardman P: Clin Oncol (R Coll Radiol) 2007; 19: 397- 417). However, most clinical trials have failed to demonstrate significant efficacy using these sensitizers, mainly because of undesirable side effects such as neurotoxicity (Kaanders J. H., Bussink J, van der Kogel A. J.: Semin Radiat Oncol 2004, 14: 233-240). The activity of doped titania nanoparticles to act as radiosensitizers under normoxic conditions is described in Townley H. E., Rapa E, Wakefield G, Dobson P., Nanomedicine 2012; 8; 526-36. Since the generation of electrons from titania should not be dependent upon the presence of molecular oxygen we sought to investigate whether the nanoparticles still showed effective radiosensitization under hypoxic conditions.

The cancer to be treated may therefore be associated with tumour tissue comprising hypoxic tumour cells. A cancer is "associated" with tumour tissue if that tumour tissue is a feature of the cancer, i.e. if the tumour is caused by the cancer. Tumour cells which are hypoxic are tumour cells which have a lower concentration of oxygen compared with normoxic cells. Hypoxic tumour cells therefore include anoxic tumour cells, i.e. cells which have an oxygen concentration of substantially 0.0. Usually, the partial pressure of oxygen, $pO_2$, in a hypoxic cell is at least 3 mmHg below the $pO_2$ in a normoxic cell, for instance at least 10 mmHg below the $pO_2$ in a normoxic cell. Often, this results in a $pO_2$ in the hypoxic cell of less than 80 mmHg, for instance from 20 to 60 mmHg, or for example from 20 to 40 mmHg. The hypoxia may be diffusion-limited hypoxia arising from large intervascular distance in the tumour. The hypoxia may be transient 'acute' perfusion-limited hypoxia due unstable blood flow in vessels. Perfusion-limited hypoxia may occur due to embolization and it is therefore of significant benefit that the nanoparticles in the embolization particle of the invention are radiotherapeutically active under hypoxic conditions.

The invention further provides a pharmaceutical composition as defined herein for use in the treatment of cancer as defined herein in combination with X-ray radiation or proton beam radiation.

In the treatment of cancer according to the invention, the embolization particles have the combined effect of embolizing the tumour as well as radiotherapeutically treating the tumour through production of ROS. The embolization particles accumulate in the vasculature of the tumour. This both embolizes the tumour and also fixes the particles in place in the tumour allowing accurate treatment of the tumour (or cancer site) using X-rays (or a proton beam).

Treatment of cancer in combination with X-ray radiation typically comprises:
  a) parenterally administering the composition or the pharmaceutical composition to a subject to be treated; and
  b) directing X-ray radiation at a locus or site of the cancer or tumour tissue.

Treatment of cancer in combination with proton beam radiation typically comprises:
  a) parenterally administering the composition or the pharmaceutical composition to a subject to be treated; and
  b) directing proton beam radiation at a locus or site of the cancer or tumour tissue.

Typically, the step of directing X-ray or proton beam radiation to a locus or site of the cancer or tumour tissue is performed directly after administering the particles to a subject by injection. In some instances, it may be necessary to allow a short period of time for the particles to spread throughout the tumour tissue, cancer site or vasculature before directing X-ray or proton beam radiation to the locus. In general, the step of directing X-ray radiation (or proton beam radiation) to a locus or site of the cancer or tumour tissue is carried out within 1 hour after administering the particle or the pharmaceutical composition to the subject. Preferably, the step of directing X-ray or proton beam radiation to a locus or site of the cancer or tumour tissue is carried out within 45 minutes after, more preferably within 30 minutes after, particularly within 15 minutes after, especially within 10 minutes after, even more preferably within 5 minutes, or immediately after administering the particle or the pharmaceutical composition to the subject.

The composition administered to the subject typically comprises a total number of embolization particles of from 10 to $10^6$, or from 20 to 10000. Often, the composition administered comprises from 20 to 1000 embolisation particles, for instance from 40 to 400 embolisation particles.

Generally, the subject is exposed to a total X-ray dose of from 1 to 200 Gy or 20 to 70 Gy, such as for example 40 to 50 Gy. An individual X-ray dose may be from 0.1 to 10 Gy. Typically, a treatment or method for treating cancer of the invention comprises directing a 1.0 to 3.0 Gy, preferably 1.5 to 2.5 Gy dose, more preferably a 1.8 to 2.0 Gy dose of X-ray radiation to a locus or site of the cancer or tumour tissue. Such small frequent doses are intended to allow healthy cells time to grow to repair any damage caused by the radiation. The proton beam radiation dose may be from 1 to 2000 Gy, 1 to 500 Gy or any of the does given above.

Typically, the X-ray radiation in a treatment or method for treating cancer of the invention has an energy from 0.005 MeV to 10 MeV. Higher energy X-rays (e.g. greater than 1 MeV) may sometimes be referred to as gamma rays. The X-ray radiation may have an energy of from 0.005 MeV to 1 MeV, or from 0.05 MeV to 0.2 MeV. For instance, the treatment of cancer according to the invention may use X-ray radiation having an energy of greater than or equal to 0.01 MeV. Alternatively, the treatment may use proton beam radiation having an energy of greater than or equal to 1 MeV, for instance from 70 to 250 MeV. The energy of the X-ray radiation used in the treatment of cancer is typically greater than or equal to 0.05 MeV, for instance greater than or equal to 0.06 MeV or greater than or equal to 0.06 MeV. The X-ray energy for treating cancer may be from 0.04 to 0.1 MeV or from 0.06 to 0.09 MeV. The energy of the X-rays used for cancer treatment according to the invention typically have an energy higher than that used for imaging purposes.

The step of directing X-ray radiation or proton beam radiation at the locus or site of the cancer or tumour tissue typically excites the metal oxide in the nanoparticles in the embolisation particles at the locus or site of the cancer or tumour tissue to generate reactive oxygen species at the locus or site of the cancer or tumour tissue.

The method may also comprise a step of detecting the presence or absence of a particle or particles of the invention at a locus or site of the cancer or tumour tissue before directing X-ray radiation to a locus or site of the cancer or tumour tissue. Typically, the step of detecting the presence or absence of the particle or particles at a locus or site comprises directing X-rays at the locus or site to obtain an X-ray image. The X-ray image may then be used to determine if a cancer or tumour tissue is present or absent at the locus or site. For diagnostic uses, the exposure time of a subject to X-rays is generally from one second to 30 minutes, preferably from one minute to 20 minutes and more preferably from one second to 5 minutes.

Treatment of cancer in combination with X-ray radiation (or proton beam radiation) may for instance comprise:
  a) administering, preferably parenterally administering, the composition or the pharmaceutical composition to a subject to be treated;
  ai) allowing the embolization particles to accumulate at a locus or site of the cancer or tumour tissue;
  aii) optionally detecting the presence or absence of the embolization particles at the locus or site of the cancer or tumour tissue; and
  b) directing X-ray radiation (or proton beam radiation) at the locus or site of the cancer or tumour tissue.

The embolization particles typically accumulate at the locus or site of the cancer or tumour tissue by embolizing vasculature within the locus or site of the cancer or tumour tissue. This both restricts blood flow to the tumour and places the embolization particles within the tumour in a suitable position to radiotherapeutically treat the cancer on exposure to X-rays or a proton beam. Thus, the treatment of cancer in combination with X-ray radiation (or proton beam radiation), in accordance with the present invention, typically comprises a step of allowing the embolization particles to embolize vasculature within a locus or site of the cancer or tumour tissue. Indeed, step (ai) of the embodiment described in the preceding paragraph may comprise: allowing the embolization particles to accumulate at a locus or site of the cancer or tumour tissue and to embolize vasculature within said locus or site of the cancer or tumour tissue.

Step (a) typically comprises intravenously administering the plurality of embolization particles or the pharmaceutical composition to the subject to be treated.

Preferably, step (a) comprises intravenously administering the plurality of embolization particles or the pharmaceutical composition into the blood stream of the subject to be treated at a location at or before the locus or site of the cancer or tumour tissue. The term "before the locus or site of the cancer or tumour tissue" as used herein means upstream in the blood flow from the locus or site of the cancer or tumour tissue, i.e. at a location in the vasculature where blood is flowing away from the heart and towards the site or locus of the cancer or tumour tissue.

The embolization particles could also be used in concert with doped nanoparticles as defined herein injected directly into the body of the tumour.

The invention also provides a method for treating cancer in a subject comprising: (a) administering to a subject an embolization particle as defined herein, a composition as defined herein, or a pharmaceutical composition as defined herein; and (b) directing X-ray radiation or proton beam radiation at a locus or site of the cancer or tumour tissue. This method may be as further defined for the use in the treatment of cancer described above. Typically, (a) comprises intravenously administering to a subject an embolization particle as defined herein, a plurality of embolization particles as defined herein, or a pharmaceutical composition as defined herein. Preferably, (a) comprises intravenously administering into the blood stream of the subject to be treated at a location at or before the locus or site of the cancer or tumour tissue, an embolization particle as defined herein, a composition as defined herein, or a pharmaceutical composition as defined herein.

The invention also provides the use of an embolization particle as defined herein, a composition as defined herein, or a pharmaceutical composition as defined herein, in the manufacture of a medicament for use in the treatment of cancer as defined herein in combination with X-ray radiation or proton beam radiation.

The invention also provides an embolization particle as defined herein, a composition as defined herein, or a pharmaceutical composition as defined herein, for use in a method of embolization. Embolization typically comprises intravenously administering the plurality of embolization particles or the pharmaceutical composition into the blood stream of the subject to be treated at a location at or before the locus or site of the cancer or tumour tissue.

The treatment of cancer in combination with X-ray (or proton beam) radiation may be performed in simultaneously with embolization. Thus, the invention also provides an embolization particle as defined herein, a composition as defined herein, or a pharmaceutical composition as defined herein, for use in a method of embolization in combination with the treatment of cancer as defined herein in combination with X-ray radiation or proton beam radiation.

Process for Producing the Embolization Particles

The invention also provides a process for producing an embolization particle comprising a microparticle coated with a plurality of nanoparticles, which nanoparticles comprise a metal oxide doped with one or more rare earth elements, wherein the metal oxide is titanium dioxide, zinc oxide or cerium dioxide, which process comprises:
(i) providing a microparticle;
(ii) contacting the microparticle with a plurality of the nanoparticles; and
(iii) heating the microparticle and the nanoparticles to form the embolization particle.

The embolization particle may be as further defined herein. The nanoparticles may be as further defined herein. The microparticle may be as further defined herein.

Typically, (i) comprises providing a plurality of microparticles. Typically, (ii) comprises mixing the microparticle with the plurality of nanoparticles, for instance mixing a plurality of microparticles with the plurality of nanoparticles. The microparticles and nanoparticles are usually mixed in the solid phase. Thus, a solid composition (e.g. a powder) comprising the plurality of microparticles may be mixed with a solid composition (e.g. a powder) comprising the plurality of nanoparticles. The volume of nanoparticles is usually greater than the volume of microparticles in the mixture. A greater volume of nanoparticles is desirable so that there is an excess of nanoparticles and the microparticles are fully coated before and during step (iii). The excess of nanoparticles also helps to produce individual embolization particles rather than clumps of aggregated embolization particles. The volume/volume (v/v) ratio of microparticles to nanoparticles (microparticles:nanoparticles) is typically from 1:1 to 1:20. For instance, the ratio may be from 1:5 to 1:15 or from 1:8 to 1:10 (v/v).

The embolization particles are formed by heating the combination of the microparticles to nanoparticles. This causes the nanoparticles to bind to each other and/or the surface of the microparticle to form the embolization particle. Typically, the microparticle comprises a polymer (for instance a polymer or a copolymer formed from styrene monomer units) and (iii) comprises heating the microparticle and the nanoparticles at a temperature which is above the glass transition temperature of the polymer. Typically, (iii) comprises heating the microparticle and the nanoparticles at a temperature of from 150° C. to 300° C. The temperature may be from 200° C. to 250° C., for instance about 230° C. Heating is usually performed for from 5 to 60 minutes, for instance from 10 to 20 minutes.

After the formation of the embolization particles, they are usually isolated from the mixture, for instance by sieving or by using a density gradient, to remove the larger embolization particles and to leave the excess nanoparticles.

An example of the production process is as follows. The microparticles were mixed with the nanoparticles in a ratio of from 1:5 to 1:15 (v/v). The nanoparticles were then sintered onto the surface of the microparticles by heating the mixture to from 200° C. to 250° C. This may be done in a furnace at a ramping rate of from 5° C. to 10° C. per minute. The mixture was held at from 200° C. to 250° C. for from 5 to 20 minutes. The embolization particles may then be separated from the excess nanoparticles using a sucrose density gradient containing 60% and 15% sucrose and centrifuging (for instance 1 hour at 9,000 rpm). The band containing the coated microparticles was extracted, centrifuged and washed. Finally the prepared particles were dried overnight under vacuum. The nanoparticles used in the invention could be added to the surface of the microparticles either concomitant to synthesis or post-synthesis.

Alternatively, step (iii) may comprise adding a composition to the microparticles and nanoparticles, which composition binds the nanoparticles to the surface of the microparticle. The added composition may be an adhesive composition, for instance a solution of polyvinylalcohol, an epoxide, a urethane, or a methacrylate. The added composition may be a resin composition.

The invention also provides an embolization particle obtainable by a process for producing an embolization particle as described herein.

The invention is described in further detail by the following Examples.

EXAMPLES

Production of Doped Nanoparticles

Nanoparticles comprising titania doped with the rare earth gadolinium were prepared. The method of production of these particles was as follows.

Gadolinium (III) nitrate hexahydrate was suspended in 10 mL of titanium (IV) isopropoxide and then 30 mL dry isopropanol was added.

The amount of rare earth metal compound that is suspended in the solution determines the amount of dopant that is introduced into the host lattice of titanium dioxide. A total amount of up to 25 mol % of one or more rare earth elements may be introduced into the host lattice of the titanium dioxide. As an example, 34 micromoles of gadolinium nitrate were added to 340 millimoles of titanium isopropoxide to produce titanium dioxide particles doped with 1 mol % gadolinium.

The solution was then added drop wise to 500 mL of a 50/50 (v/v) water/isopropanol mix whilst stirring vigorously. The mixture was stirred for a further 5 minutes and the precipitate then allowed to settle. The supernatant was removed and the precipitate washed with 200 mL isopropanol and stirred for a further 10 mins. The supernatant was subsequently collected by filtration and then autoclaved in tubes half-filled with $ddH_2O$. The slurry was then kept at 100° C. until dry. Samples were ground to a fine powder and subsequently fired at various temperatures (e.g. 3 hours at 700 ° C.).

The above method may be used to prepare other rare earth doped titanium dioxide particles when alternative rare earth metal nitrate compounds are used. The above method may also be used to prepare rare earth doped cerium oxide or zinc oxide when a cerium or zinc ketonate, such as zinc acetylacetonate or cerium acetylacetonate, is used as the starting material.

Figure 2:
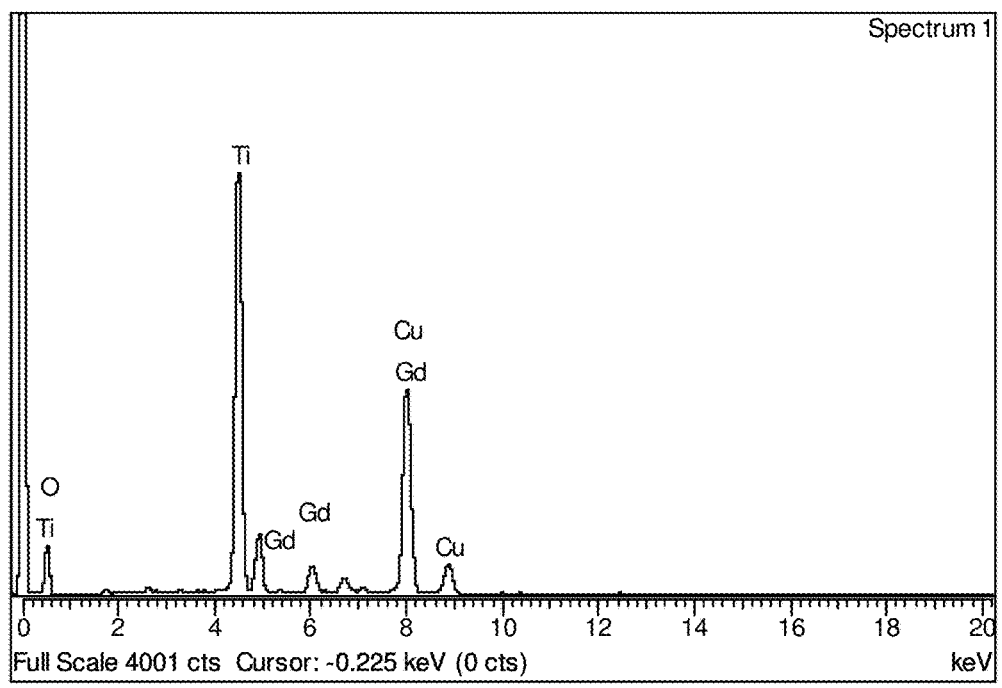
FIG. 2 shows energy-dispersive X-ray (EDX) spectroscopy results showing the presence of gadolinium in doped titania nanoparticles.

TEM images show the size and size distribution of titania nanoparticles doped with gadolinium (FIG. 1; upper) and their crystallinity (FIG. 1; lower). The EDX trace (FIG. 2) confirms the presence of gadolinium in the titania nanoparticles.

The doped nanoparticles were also synthesised using flame spray pyrolysis (FSP) to confirm that this method was also possible. In a typical experiment, the appropriate amounts of titanium and gadolinium precursor(s) for a 5 at % Gd in $TiO_2$ were added to a solvent and stirred for 1 hour. The solution was sprayed through a nozzle. The spray was defined by the speed of the precursor injection and the $O_2$ dispersion gas rate and was ignited with a pilot flame made of methane and oxygen set at 1.5 and 3.2 L/min respectively. The powder resulted from the combustion of the precursors and was collected under vacuum onto a glass fibre filter paper. Finally, the white powder was fired at 500° C. for 2 hours.

Arsenazo III Assay On Doped Nanoparticles

Titania nanoparticles doped with 5% gadolinium prepared by FSP were coated with silica ($TiO_2$@5% Gd (FSP)@Si) and analyzed for gadolinium leaching using the Arsenazo III assay. The sample was resuspended in Milli-Q water, sonicated and filtered. The sample was diluted (1:401) and three UV-VIS spectra were collected for the sample. Absorbance values at 300 nm were determined. Based on a calibration curve for P25, the initial concentration of the sample after filtration was calculated (5.45 mg/mL). 500 μL of the sample was injected into Slide-A-Lyzer Dialysis Cassette (ThermoScientific) and dialyzed against Milli-Q water (55 mL) with constant stirring at room temperature. Gadolinium (III) nitrate hexahydrate was used as a source of free gadolinium in a positive control experiment. 500 μL of the gadolinium (III) chloride hexahydrate (0.788 mg/mL) was injected into Slide-A-Lyzer Dialysis Cassette (ThermoScientific) and dialyzed against water (55 mL) with constant stirring at room temperature. Additionally, 500 μL of uncoated TiO2@5% Gd(FSP) (5.45 mg/mL) sample was injected into Slide-A-Lyzer Dialysis Cassette (ThermoScientific) and dialyzed against water (55 mL) with constant stirring at room temperature.

The water ("Sink") was assessed for free gadolinium after 1 day of dialysis, and up to 14 days. Samples for measurement were prepared by mixing 100 μL 0.2 mM Arsenazo III and 900 μL sink. Blanks were prepared by mixing 100 μL 0.2 mM Arsenazo III and 900 μL Milli-Q water. All sink samples were collected for further analysis in by inductively coupled plasma mass spectrometry (ICP-MS).

Microparticles

Figure 3:
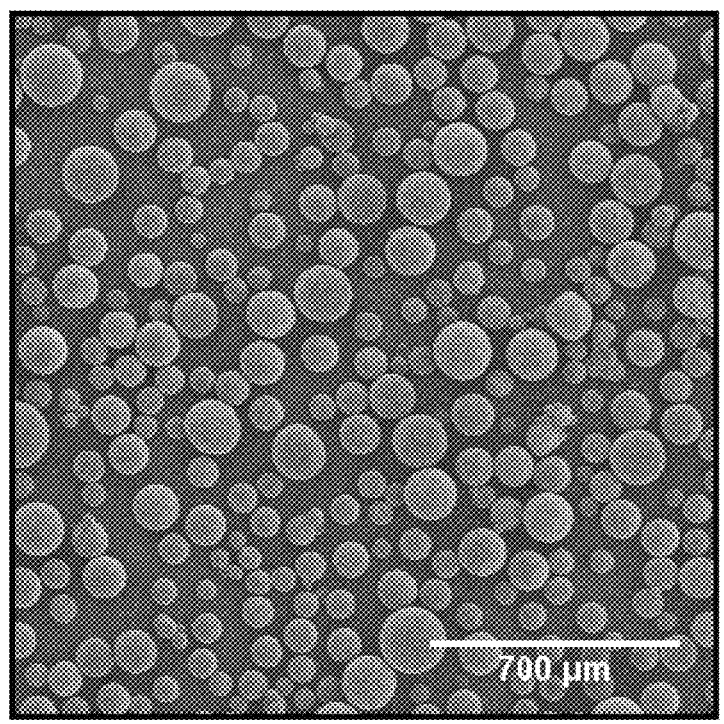
FIG. 3 shows a scanning electron micrograph (SEM) of polystyrene microparticles synthesized in the laboratory to give a range of sizes.
Figure 4:
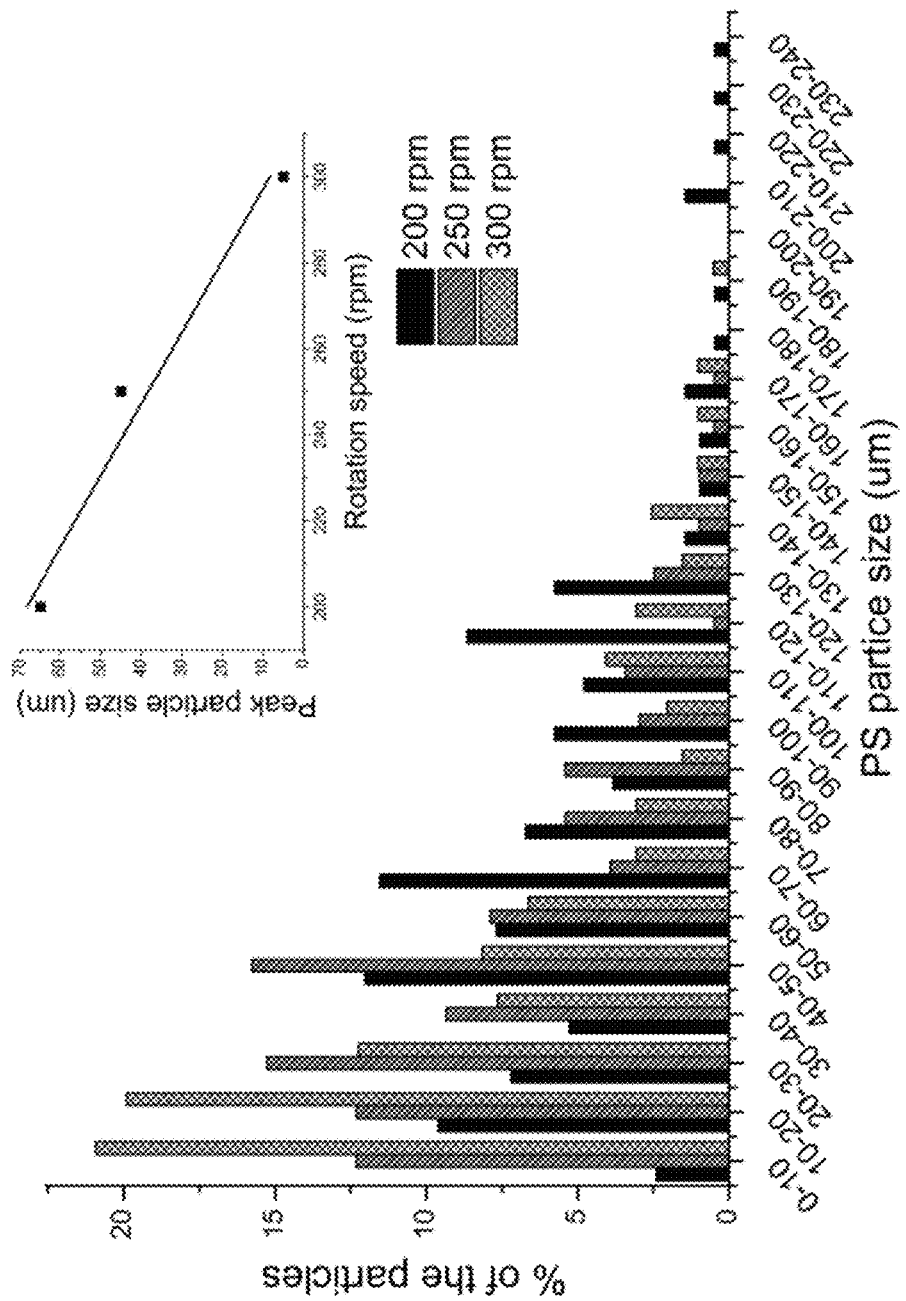
FIG. 4 shows quantification of the range of sizes of polystyrene microparticles synthesized in the laboratory.

Polystyrene microparticles can either be prepared in the laboratory or commercial standards may be used. The microparticles can be made or bought as a range of sizes. The size of the blood vessels to be blocked will range in diameter from the main blood vessels supplying the tumour to the smaller internal vessels (see Table 1 above). The microparticles can therefore be applied as a heterogenous collection of diameters (FIGS. 3 and 4) or as a more tightly controlled diameter (FIG. 5), depending upon the exact application and intended point of blockage.

Polystyrene microparticles were either synthesised in the laboratory or purchased from Duke scientific as dry green fluorescent 40 μm polystyrene divinylbenzene beads. The synthesis of the polystyrene microparticles was carried out by the suspension copolymerisation of styrene and ethylene glycol dimethacrylate (EGDMA), as previously described in Ihara H et al. (Materials Chemistry and Physics. 2009;114 (1):1-5) and Uchimura A, et al. (Materials Chemistry and Physics. 2011;129(3):871-80). An oil phase was created by mixing 2.5 ml of styrene (Aldrich), 2.5 ml of EGDMA (Aldrich) and 50 mg of azobisisobutyronitrile (AIBN; Aldrich). The oil phase was then added to 30 ml of aqueous 4 wt. % polyvinyl alcohol (PVA, 87-90% hydrolyzed, average molecular weight 30,000-70,000; Aldrich) in a round bottomed flask. The mixture was stirred at 250 rpm for one hour at room temperature and then left to stand for 24 hours at 60° C. The particles were collected by centrifugation, washed in $ddH_2O$ twice, re-suspended in 30 ml $ddH_2O$ and refluxed overnight to remove any remaining PVA. The particles were then collected by centrifugation, washed with methanol twice and dried under vacuum.

Production of Embolization Particles

The laboratory-synthesized polystyrene microparticles and the purchased polystyrene divinlybenzene microparticles were each coated with the gadolinium doped titania nanoparticles.

The microparticles were mixed with the nanoparticles in a 1:9 ratio (v/v). The titania nanoparticles were then sintered onto the surface of the polystyrene microparticles by heating the mixture to 230° C. which is above the glass transition temperature of the polystyrene microparticles. This was done in a Carbolite RWF 1200 furnace at a ramping rate of seven degrees per minute. The mixture was held at 230° C. for 15 minutes to limit any potential change in crystal phase of the doped titania nanoparticles. The doped titania nanoparticle coated microparticles were separated from the excess nanoparticles using a sucrose density gradient containing 60% and 15% sucrose and centrifuging for one hour at 9,000 rpm. The band containing the coated microparticles was extracted, centrifuged and washed in ddH$_2$O three times to remove sucrose. Finally the prepared particles were dried overnight under vacuum.

TEM was used to measure the size, surface morphology and crystal structure of the gadolinium doped titania nanoparticles. TEM was performed using a JEOL JEM-2010 microscope equipped with a LaB$_6$ thermionic electron gun operating at a primary beam energy of 200 keV and an Oxford Instruments INCA X-ray analysis system for carrying out energy dispersive X-ray spectroscopy (EDX). By analysing the characteristic X-rays produced by the interaction of the primary electron beam with the sample, the elements present in the sample could be determined. TEM specimens were prepared by re-suspending the nanoparticles in ethanol and drop casting onto holey carbon coated grids (Agar Scientific).

SEM was used to evaluate the size distribution and surface coverage of the nanoparticle coated microparticles (i.e. the embolization particles of the invention). SEM was performed using a JEOL JSM-840F microscope operating at a primary beam energy of 3 keV and images were collected in secondary electron imaging mode. SEM specimens were prepared by dusting onto a carbon taped SEM stub (Agar Scientific) and then coated with a 3 nm layer of platinum to reduce charging during operation.

Figure 5:
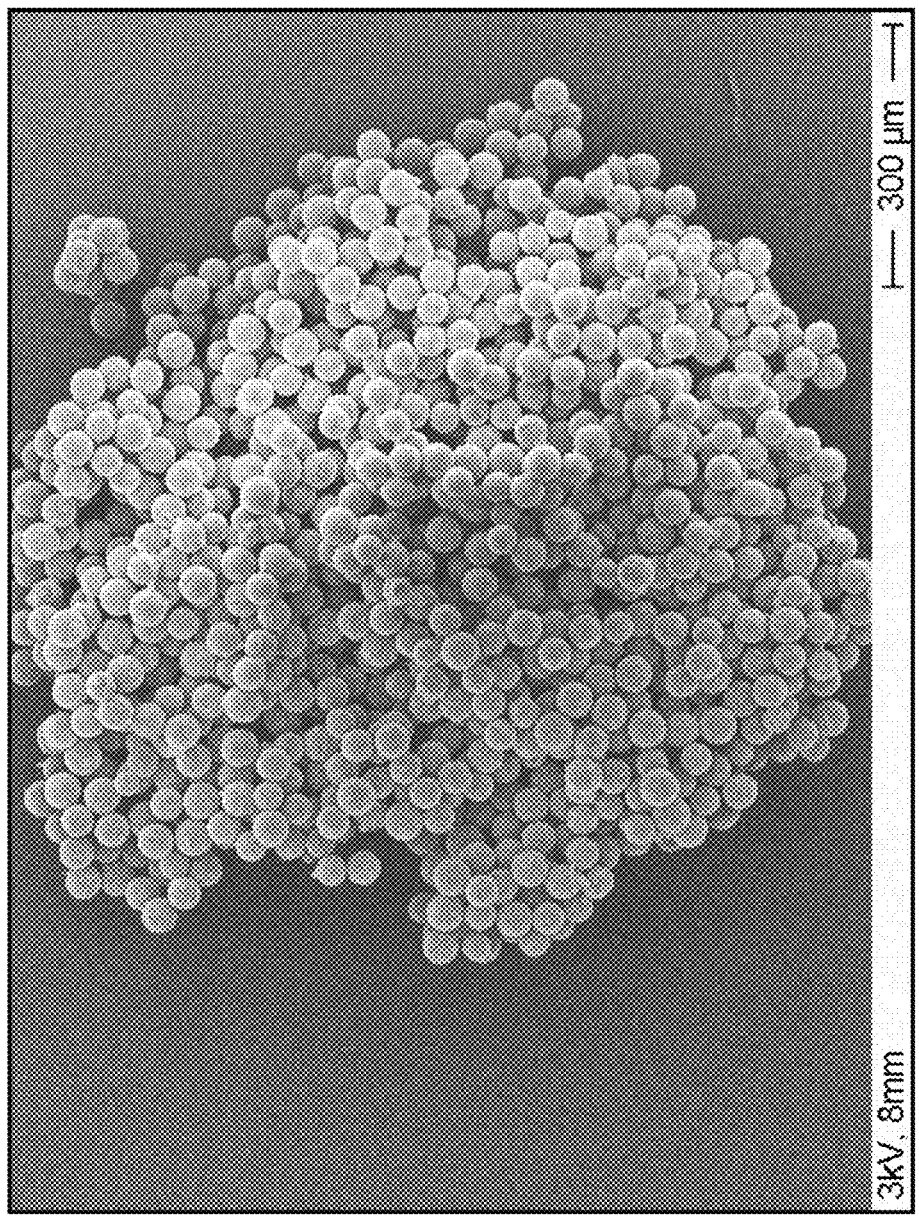
FIG. 5 shows an SEM image showing commercial fluorescent 39 μm polystyrene microparticles which have been coated with doped titania nanoparticles.
Figure 6:
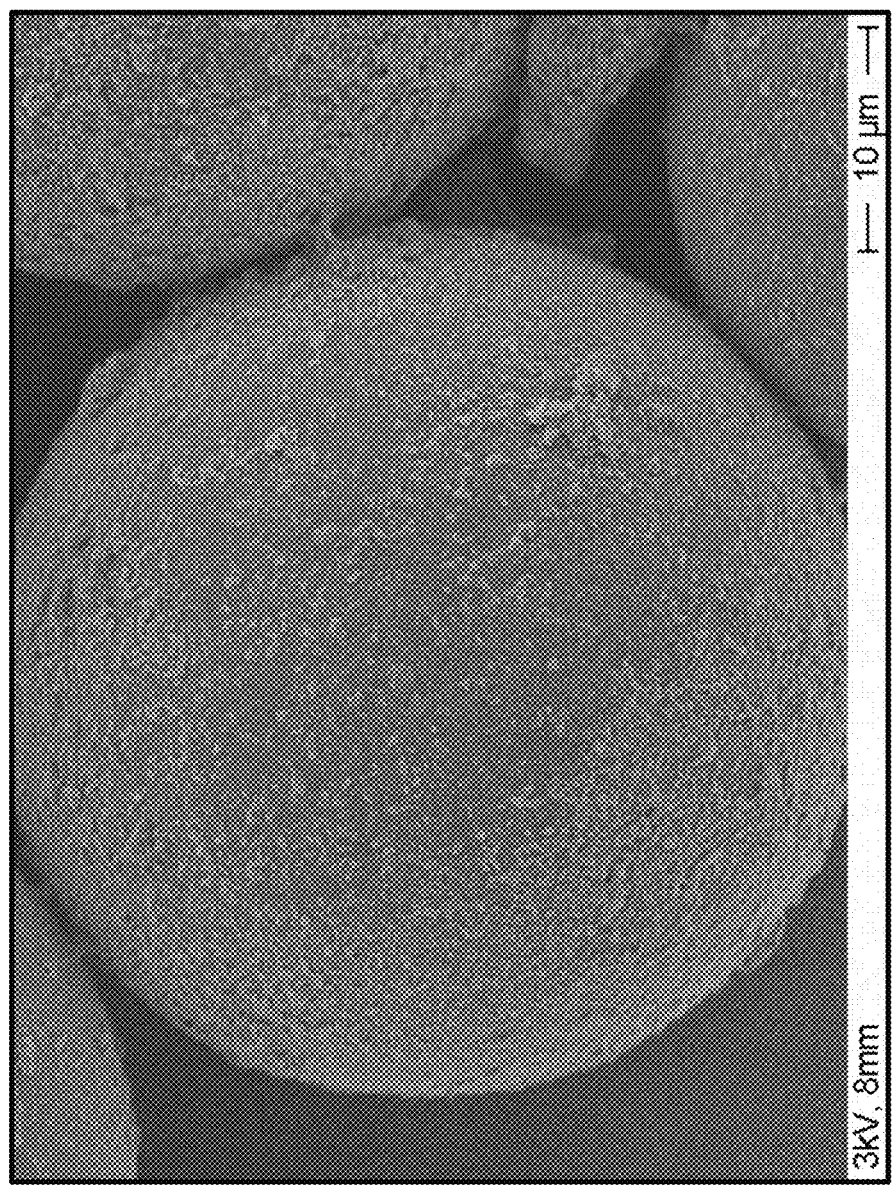
FIG. 6 shows a high resolution SEM image of polystyrene microparticles coated with doped titania nanoparticles.

SEM images of embolization particles according to the invention are shown in FIGS. 5 and 6. The nanoparticles can be visualized on the surface of the microparticles in FIG. 6, which shows that the nanoparticles provide an even coating which would not disrupt the ability of the microparticle to embolize vasculature.

Cell Death Experiments—Example 1

The effectiveness of the nanoparticles and the nanoparticle coated microparticles was determined in vitro using a rhabdomyosarcoma (RD) cell line. Cells were grown in growth medium (Dulbecco's Modified Eagle's Medium (DMEM); Aldrich) supplemented with 10% fetal calf serum (Aldrich), 2 mM L-Glutamine (Aldrich), 100 U/ml Penicillin (Aldrich) and 0.1 mg/ml Streptomycin (Aldrich) and incubated at 37° C. in a 5% CO$_2$ atmosphere. Cells were passaged every three to four days.

Figure 7:
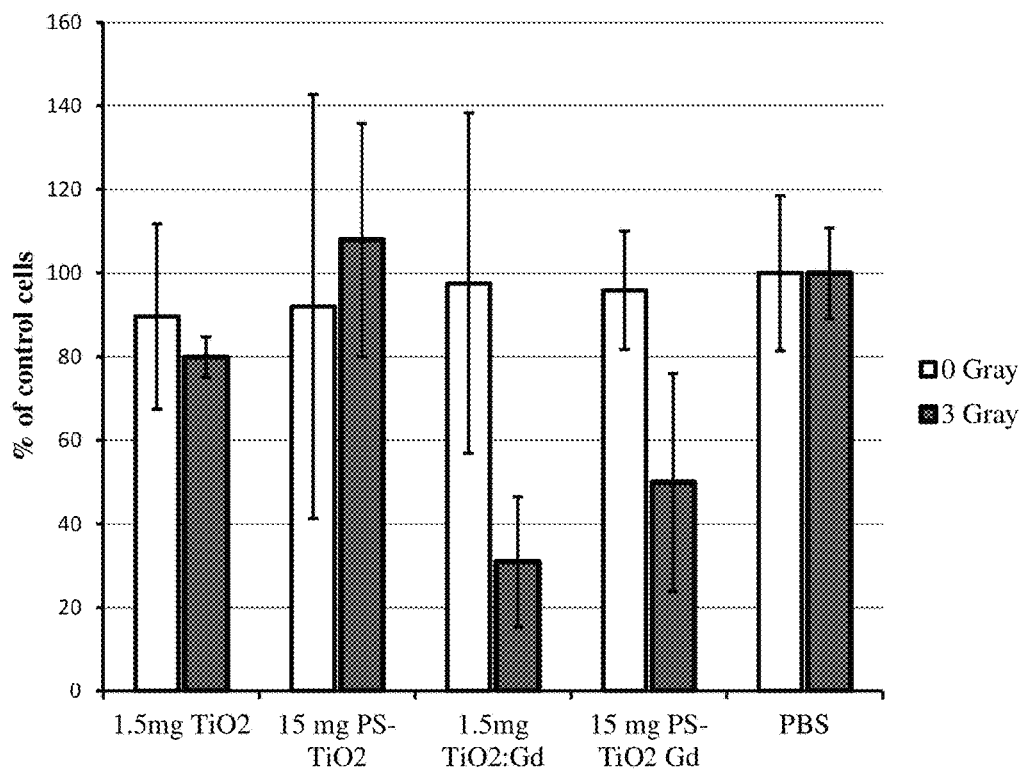
FIG. 7 shows cell death results before (0 Gray) and after (3 Gray) X-ray exposure for rhabdomyosarcoma cells which were incubated with either doped ($TiO_2$—Gd) or undoped ($TiO_2$) titania nanoparticles as either free nanoparticles or nanoparticles bound to polystyrene (PS), or incubated with PBS as a control. All samples are normalized to the control.

RD cells were seeded on two separate 96 well plates at 1×10$^4$ cells per well in 150 µl of fresh media and incubated overnight to allow the cells to adhere to the plate. The following day both plates of cells were treated, in triplicate, with: (i) 1.5 mg of undoped titania nanoparticles (1.5 mg TiO$_2$); (ii) 1.5 mg gadolinium doped titania nanoparticles (1.5 mg TiO$_2$:Gd); (iii) 15 mg of microparticles coated with undoped titania nanoparticles (15 mg PS-TiO$_2$); (iv) 15 mg of microparticles coated with gadolinium doped titania nanoparticles (15 mg PS-TiO$_2$:Gd); or (v) phosphate buffered saline (PBS) as a control. The next day one plate of particle-treated cells was exposed to a broad spectrum of X-ray energies up to 150 keV with and average energy of from 80 to 90 keV and a dose of 3 Gray while the other plate was kept unirradiated as a control (0 Gray). On the final day of the experiment, cells proliferation was determined by manual cell counting using a hemocytometer. The media was removed, cells were washed in PBS and 30 µl of Trypsin-EDTA was used to detach the adherent cells. After confirming the cells were detached, 30 µl of fresh growth media was added to neutralise the trypsin and the cells were counted using a light microscope. Cells were allowed to recover overnight, and cell death assessed by manual cell counting (FIG. 7).

The experiment shows that titania nanoparticles either alone or combined with microparticles do not cause cell death, with or without irradiation (FIG. 6; 1.5 mg TiO$_2$ and 15 mg PS-TiO$_2$). The gadolinium doped particles are inert in the absence of irradiation, but show dramatically increased cell death after irradiation.

It has been shown therefore that embolization particles may be functionalised with doped nanoparticles to produce particles which can both embolize a cancer site or tumour and cause cell death on exposure to X-ray radiation.

Cell Death Experiment—Example 2

Cell Culture

The effectiveness of the nanoparticles and the nanoparticle coated microparticles was determined in vitro on immortalized cancer cell lines obtained from the Marican Type Culture Collection (ATCC; Manassas; Va.): Rhabdomyosarcoma lines, RD (ATCC code CCL-136) and RH30 (ATCC code CRL-7763), and the cervical cancer HeLa line (ATCC code CCL-2). Cells were grown in growth medium (Dulbecco's Modified Eagle's Medium (DMEM); Aldrich) supplemented with 10% fetal calf serum (Aldrich), 2 mM L-Glutamine (Aldrich), 100 U/ml Penicillin (Aldrich) and 0.1 mg/ml Streptomycin (Aldrich) and incubated at 37° C. in a 5% CO$_2$ atmosphere. Cells were passaged every three to four days.

Clonogenic Assay

Flasks of HeLa cells were seeded and cells incubated for 4 hours to allow attachment. Nanoparticles were added to the appropriate flasks and incubated overnight prior to irradiation. Following irradiation, cells were incubated for 1 hour at 37° C. Cells were then trypsinized, counted and petri dishes seeded with 1000 cells/ dish. At least three petri dishes were seeded for each experimental condition. The cells were incubated at 37° C. in a 5% CO$_2$ atmosphere undisturbed for 2 weeks. Cells were then stained by washing twice with PBS, fixed using glutaraldehyde for 30 minutes prior to adding 0.5% crystal violet stain for at least 1 hour and surviving colonies subsequently counted (>50 cells). The surviving fraction was then calculated by dividing the colonies counted by the number of cells seeded and correcting for the plating efficiency determined using the 0 Gy control.

Cell Proliferation After Incubation With Radiosensitizing Embolization Microparticles RD cells were seeded on two separate 96 well plates at 1×10$^4$ cells per well in 150 µl of fresh media and incubated overnight to allow the cells to adhere to the plate. The following day triplicate plates were prepared for both cell types and treated with either (i) 1.5 mg of undoped titania nanoparticles, (i) 1.5 mg of gadolinium doped titania nanoparticles, (iii) 15 mg of microspheres coated with undoped titania nanoparticles, (iv) 15 mg of microspheres coated with gadolinium doped titania nanoparticles (v) PBS as a control. The next day one plate of particle treated cells was exposed to 3 Gy of x-rays while the other plate was kept unirradiated as a control. After a further 24 hours, cell proliferation was determined by manual cell counting using a hemocytometer following the removal of the adherent cells using Trpysin-EDTA.

Hypoxia
Experimental Set-up for Irradiation Under Hypoxia

Hypoxia experiments to assess cell proliferation were performed using an oxygen concentration of 0.2% in nitrogen and 5% carbon dioxide. Two hours prior to irradiation cells were moved to a hypoxia chamber which was flushed with gas of the above composition positioned on a 1 mm thick stainless steel shelf above the x-ray set. In the chamber the cells were kept at 37° C. by placing the flasks on top of a 5 mm thick aluminium plate heated by circulating warm water around the outside of the plate. Following irradiation, the cells were transferred to an incubator where hypoxia was maintained. The number of live cells was evaluated by manual cell counting after a further 24 hours.

Irradiations

X-ray exposures were performed with 250 kV (constant potential) X-rays with 0.25 mm thick copper filter (half-value layer of 1.08 mm Cu) at a dose rate of 0.57 Gy/min measured using calibrated EBT3 gafchromic film (International Speciality Products, Wayne, N.J., USA). All doses quoted in the paper refer to dose to water, with samples with and without nanoparticles exposed for the same amount of time.

Production of Tantalum Oxide Radioopaque Particles

TaOx nanoparticles were prepared using the following method. An oil phase was created by mixing 2.3 g of Igepal Co-520 (Aldrich), 0.75 ml of ethanol (Fisher) and 20 ml of cyclohexane (Aldrich) by stirring. A microemulsion was then created by adding 250 µl of 2 mM NaOH (aq). Finally, 50 µl of tantalum (V) ethoxide (Aldrich) was added to the microemulsion at room temperature and incubated for 5 minutes. Ethanol (Fisher) was then added to the mixture to allow the particles to sediment. Particles were then collected by centrifugation, washed in ethanol three times and dried in a desiccator overnight.

Incorporation of Tantalum Oxide Nanoparticles Into Microparticles

Polystyrene-TaOx microparticles were prepared by a modification of the method presented by Ihara et al. (Materials Chemistry and Physics. 2009;114(1):1-5.) for the synthesis of polystyrene microparticles. Firstly, 2.5 ml of styrene (Aldrich), 2.5 ml of EGDMA (Aldrich) and 50 mg of azobisisobutyronitrile (AIBN; Aldrich) were mixed to create an oil phase. Different masses of TaOx nanoparticles were mixed into the oil phase to create PS-TaOx microparticles containing theoretically 0 wt. %, 5 wt. %, 10 wt. %, 20 wt. % and 50 wt. % TaOx nanoparticles. The oil phase was then sonicated using an ultrasonic probe (Sonic Vibra-Cell) for one minute (104 W, 5 seconds pluses with 5 second intervals) to increase the dispersion of the nanoparticles throughout the oil phase. The oil phase was added to the 30 ml of an aqueous phase containing 4 wt. % poly (vinyl alcohol) (PVA) (87-90% hydrolyzed, average molecular weight 30,000-70,000; Aldrich) in a round-bottomed flask. The mixture was stirred for one hour at room temperature and then left to stand for 24 hours at 60° C. The particles were collected by centrifugation, washed twice in ddH$_2$O, then re-suspended in 30 ml ddH$_2$O and refluxed overnight to remove any remaining PVA. The particles were finally collected by centrifugation, washed twice with methanol and dried under vacuum.

Results
Doped Titania Nanoparticles
Flame Spray Pyrolysis Synthesis Route

The doped titania nanoparticles can be prepared by the sol-gel process described above. An alternative FSP method was also used which has the benefit of being more suitable for large scale production of the nanoparticles for clinical applications. FSP synthesis is a promising technique for fast and scalable synthesis of nanoparticles. Precursors are dissolved/dispersed in a highly exothermic solvent and combusted in a flame. It is commonly used in industry as large quantities of product can be prepared with no aqueous by-product. The mechanism of particle formation is based on a gas-to-matter principle and can be divided into four main steps: (i) precursor spray evaporation/decomposition forming metal vapour, (ii) nucleation as a result of super-saturation, (iii) growth by coalescence and sintering, and (iv) particle aggregation/agglomeration.

A series of doped Gd-TiO$_2$ nanoparticles were prepared by this method and the results presented here are for the 5 at % gadolinium doped sample. TEM, EDX and XRD analyses were carried out on the synthesized nanoparticles. The TEM images show the nanoparticles to be of a spherical nature, with a particle size of 5-20 nm. XRD analysis revealed the presence of both the anatase and rutile phases with a crystallite size around 6-8 nm for anatase and 10-12 nm for rutile. No additional crystalline phase other than rutile and anatase are discernible although other Gd phases may still be present (diffractometer resolution may be too low to detect any peaks at such small concentrations). Furthermore, no significant shift in the anatase or rutile peaks was detected, as one would expect when considering the cation sizes in a [6] fold coordination of the rare earth (rGd$^{3+}$=0.938 Å compared to rTi$^{4+}$=0.605 Å). It was found that furnace calcination in air at 500° C. aiming to remove any carbon residue did not change the particle size and rutile/anatase ratio. According to HAADF images, Gd is present at the surface of the nanoparticles, although the resolution is limited. The XPS spectrum of the 5%-doped sample concurs with this supposition as it shows the presence of Gd. ICP-MS results showed that the Gd content of the FSP produced materials correlated well with NPs with theoretical Gd content of 10.4 wt % Gd 48.4 wt % Ti.

Integrity of Nanoparticles

Since free gadolinium has the potential to be toxic in patients it was tested whether any free gadolinium was released from the surface of the nanoparticles. Nanoparticles were incubated in water for a period of 14 days and the sink solution assessed for free gadolinium at 1, 5, 6, 8 and 14 days. Gadolinium (III) nitrate hexahydrate was used as a positive control in the assay due to its solubility. Using the arsenazo assay, no gadolinium was detected from sink solution collected from samples containing the nanoparticles. Due to the limits of detection of the arsenazo assay, the same sink samples were also analysed by ICP-MS. Here the detection limit is <0.01 ppm but again no gadolinium was detected, indicating that the nanoparticle structures is not changed by incubation in aqueous solution and that the nanoparticles maintain their integrity.

Radiosensitizing Properties of the Nanoparticles

Figure 8:
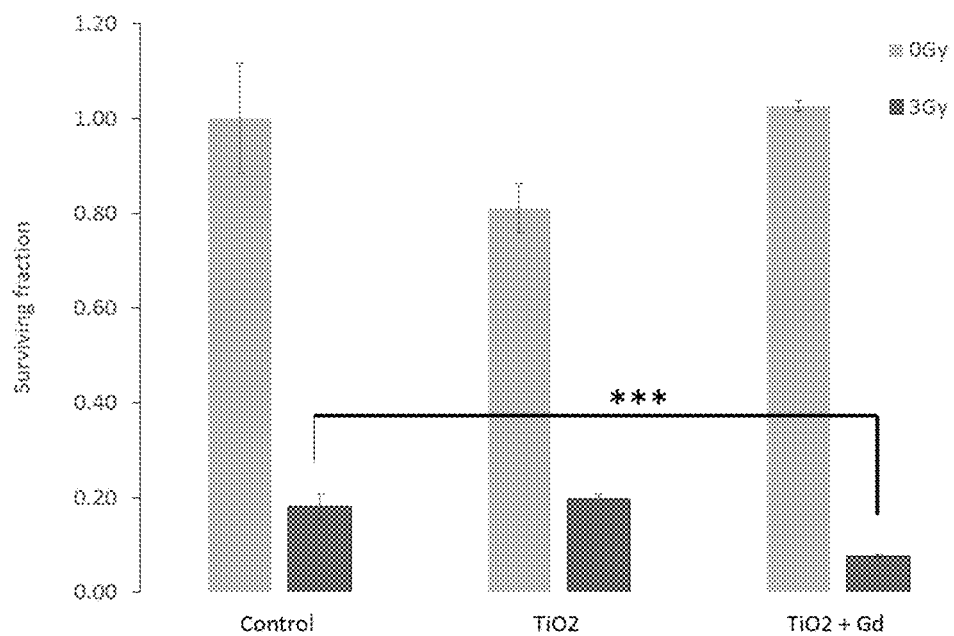
FIG. 8 shows the effect of doped titania nanoparticles on the clonogenic survival of HeLa cells following 3Gy irradiation.

The ability of the nanoparticles to act as radiosensitizers was verified using the clonogenic assay. The HeLa cell line was used since our experimental RD and RH30 cell lines do not form colonies well. The variation in surviving fraction (determined from colonies counted and corrected for the plating efficiency, PE) as a function of dose and nanoparticle treatment is shown in FIG. 8. In the absence of irradiation there was no significant difference between the controls ($PE_{con}=0.88\pm0.10$) and either the undoped ($PE_{undoped}=0.72\pm0.04$) or doped titania ($PE_{doped}=0.90\pm0.009$). After irradiation with 3 Gy there was no significant difference between the number of colonies seen in the sample with no nanoparticles and those incubated with titania nanoparticles. However, it can be seen that there was a highly significant ($p\leq0.05$) difference between samples incubated with no nanoparticles compared to those incubated with doped titania nanoparticles. This confirms that doped titania nanoparticles prepared by FSP are capable of radiosensitizing in a similar fashion to those prepared by sol-gel, and therefore provides a methodology for the large scale production of these nanoparticles for radiobiological testing and clinical use.

Radiosensitizing Under Hypoxic Conditions

To further investigate the ability of the particles to act as radiosensitizers under clinically relevant conditions nanoparticles were introduced in to cells under true hypoxia with the cells incubated and irradiated under reduced oxygen conditions.

Hypoxia

Figure 9:
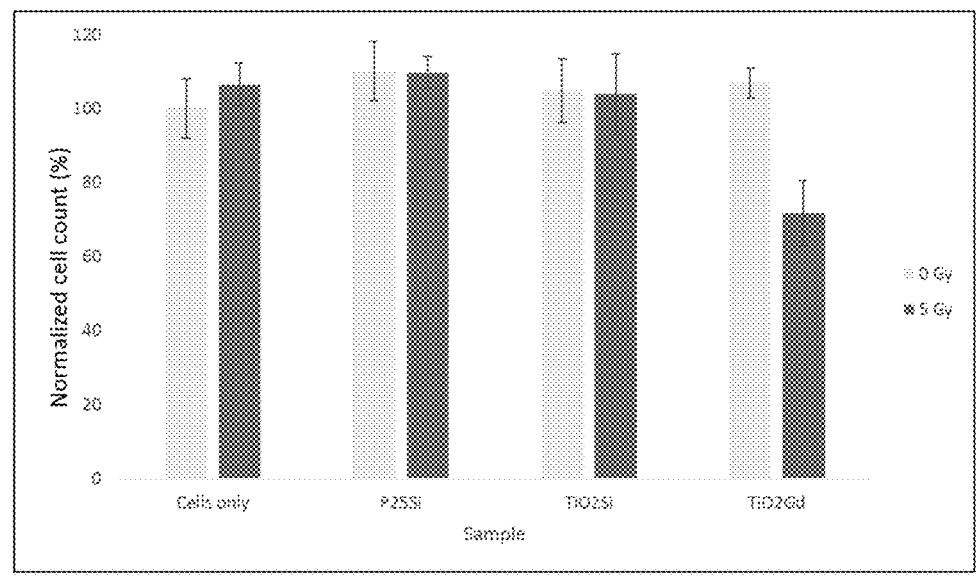
FIG. 9 shows the effect of incubation under hypoxic conditions (0.2% $O_2$) on cell proliferation in the presence of titania nanoparticles.

While the hypoxia mimetic agents can activate similar signalling pathway in cells similar to those observed as a result of hypoxia, it does not prevent the oxygen present in the cell from directly modifying the radiation induced DNA damage, which is believed to be the dominant mechanism for the oxygen effect. It was therefore also important to investigate the action of the particles in cells cultured under reduced oxygen conditions. The experimental proliferation data for RH30 cells cultured in the absence of nanoparticles performed under hypoxic conditions showed no significant difference in cell number following an exposure of 5 Gy compared to an unirradiated control (FIG. 9). Similarly cell counts were also observed when the cells were incubated with the standard control (P25@Si) and $Tio_2$@Si nanoparticles prepared by FSP when exposed to either 5 Gy irradiation or unirradiatied. Conversely, while cells incubated with the TiO2@Gd@Si radiosensitizer nanoparticles show no difference in the absence of radiation (as expected), after irradiation a significant decrease of 29% ($p\leq0.05$) in the cell count was observed.

Incorporation of TiO2: Gd Nanoparticles Into Embolization Microparticles

Nanoparticle Coating of Polystyrene Microparticles

Polystyrene microparticles were either prepared in the laboratory, or commercial standards used, in a range of sizes. The size of the embolization particles was varied since there will be a range in the diameter of the vessels supplying blood to the tumour.

Figure 10:
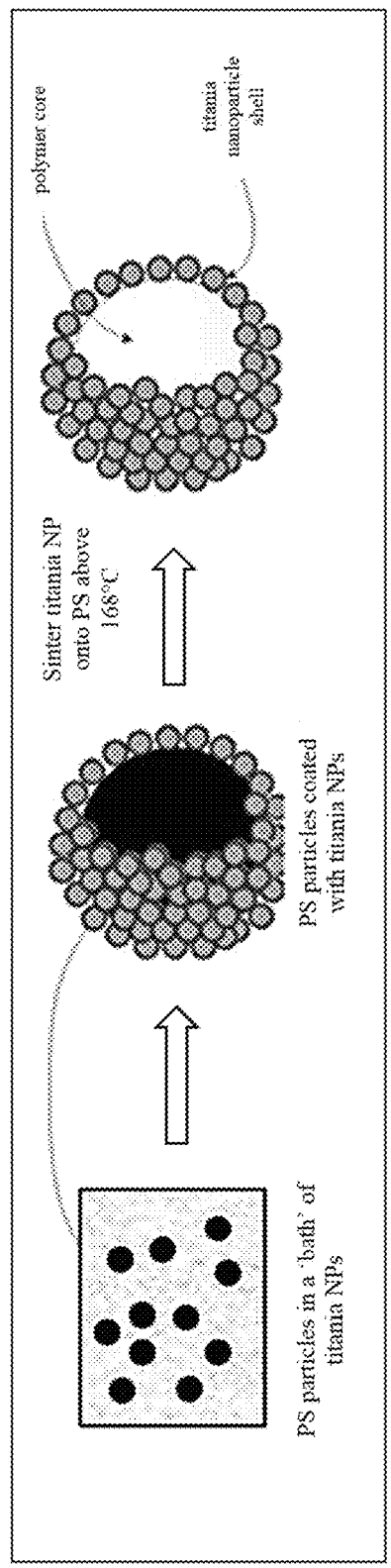
FIG. 10 shows a schematic of a method for forming an embolization particle according to the invention.

The bland embolization particles were coated with either control titania nanoparticles or doped titania nanoparticles. A number of methods were investigated but the most successful was found to be sintering the titania nanoparticles onto the polystyrene, as shown in FIG. 10. The coating of the microparticles with nanoparticles was assessed by SEM.

Radiosensitizing Properties of Embolization Particles

Figure 11:
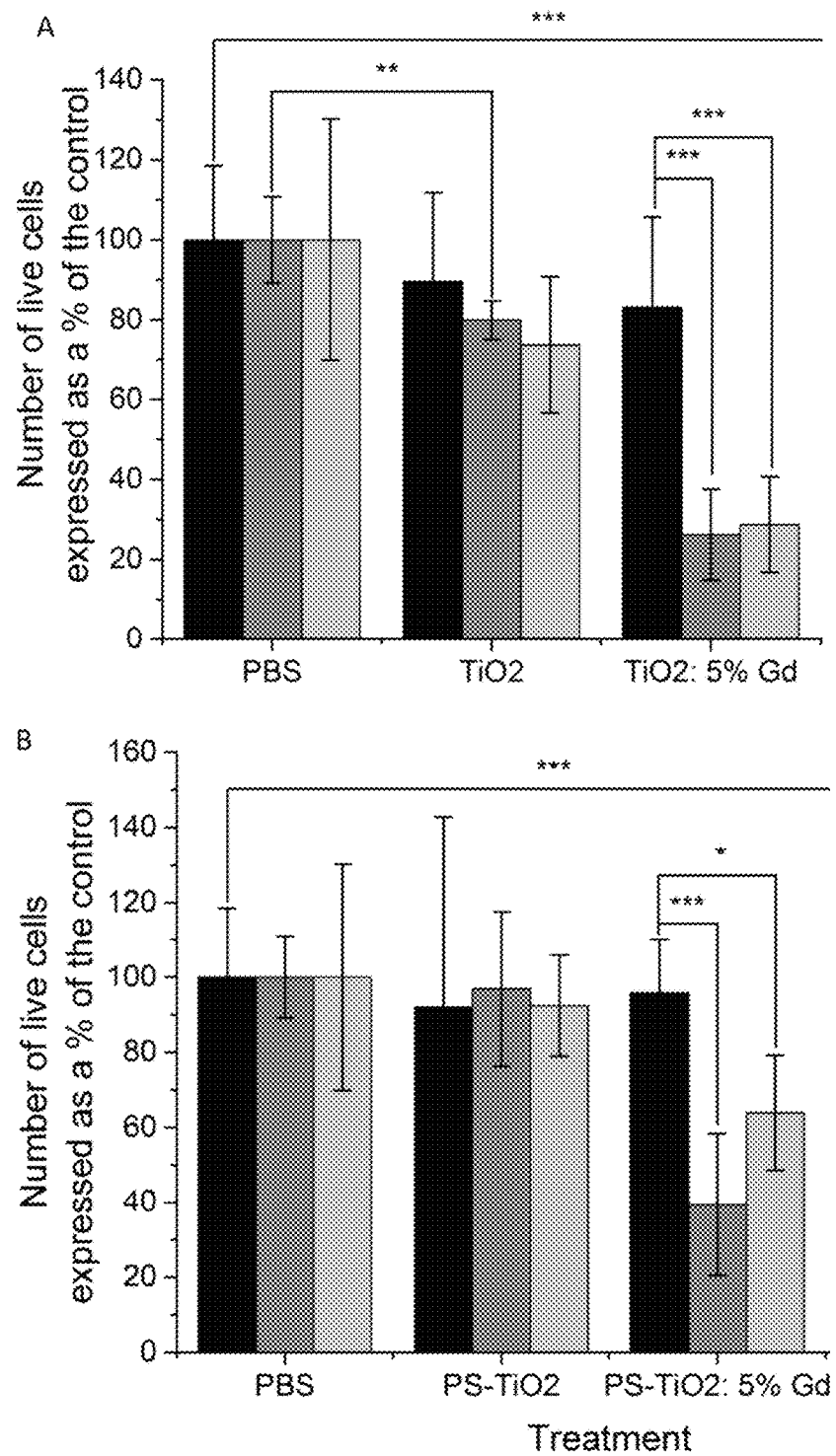
FIG. 11 shows that doped titania nanoparticles are still efficient radiosensitizers after coating embolic particles.

Radiosenitization of titania coated embolization particles was tested in cell culture using a proliferation assay. It can be seen that in the unirradiated control samples, neither titania nanoparticles alone or polystyrene microparticles coated with titania nanoparticles were able to significantly effect cell count (FIG. 11). Equally the gadolinium doped titania nanoparticles did not significantly effect cell number in the unirradiated controls.

Conversely, it was confirmed that both the gadolinium doped nanoparticles and the microparticles coated with the gadolinium doped titania nanoparticles were able to produce a significant reduction in cell number following irradiation (compared to undoped nanoparticles where no significant difference was observed). Therefore embolization microparticles coated with Gadolinium doped titania nanoparticles would be expected to act as radiosensitizers in addition to acting as a physical block of nutrients and oxygen to the tumour.

Discussion

Nanoparticle Synthesis and Characterization

Herein is described: a scalable method for the production of radiosensitizing doped titania nanoparticles; demonstration of the integrity of the nanoparticles; investigation of their efficacy under hypoxic conditions, and demonstration of further utility as a component of embolization microparticles.

Herein is described the use of FSP to generate the nanoparticles. The powders have 15-100 nm average particle sizes (APS) with specific surface areas of 30-100 $m^2/g$. The FSP technology can be used to produce mixed and single metal oxides easily from low cost starting materials in a single step. Uniform particle size distributions are obtained as it is a vapor phase process. Metal carboxylates or alkoxides, are often used as precursors and thus limited metal impurities or other unwanted contamination such halides would be found in the end product. Finally, the process has been shown to be scalable and products are already available commercially.

The nanoparticles synthesized here were shown to be between 7.9 and 11.7 nm in diameter with anatase particles being smaller than rutile particles, and the presence of the gadolinium dopant confirmed by EDX. The gadolinium doped nanoparticles prepared by FSP were subsequently confirmed to act as radiosensitizers in cell culture, showing a large reduction in both clonogenic survival (FIG. 8) and cell proliferation (FIG. 9). Further tests were undertaken to ensure that there was no breakdown of the structure and consequent release of the rare earth component. This was important since gadolinium in its unbound state is extremely toxic and is a potent inhibitor of calcium channels and has significant cardiovascular and neurological toxicity. Gadolinium is known to accumulate in the liver, bone, and lymph nodes; and in mice the median lethal dose (LD50) of $GdCl_3$ is only 100-200 mg/kg. However, gadolinium in its chelated form is commonly used to improve tissue contrast in MRI and has been proven to be safe in patients with normal kidney function. The data showed that there was no release of gadolinium from the nanoparticles using either the arsenazo assay recommended by the National Characterization Laboratory (USA) or by ICP-MS. Additional investigations by PIXE confirm the structural integrity of the nanoparticles have shown further evidence that there is no release of rare earth elements.

Efficacy of Nanoparticles Under Hypoxia

Whilst the nanoparticles have been demonstrated to act as radiosensitizers under normoxic conditions, tumour cells are often hypoxic or anoxic. Hypoxia is one of the most important parameters that cause enhanced tumour aggressiveness and treatment resistance. This is because molecular oxygen is a potent radiosensitizer. However, this radiosensitization does not result from metabolic or physiological effects of the oxygen, but reflects the fact that oxygen is an extremely electron-affinic molecule which is involved in the chemical reaction that leads to the production of DNA damage after the absorption of energy from ionizing radiation. Oxygen deprivation can therefore result in a significant reduction in the efficiency of radiation therapy. As such, it would be pertinent to assess the efficacy of the nanoparticles under reduced oxygen conditions.

The action of the nanoparticles was investigated under true hypoxia. During radiotherapy there will be effects on proliferation and cell cycle progression, but the dominant effect of oxygen is modification of radiation induced DNA damage decreasing its repairability, and therefore low oxygen concentrations can result in a decrease in efficiency of radiation in inactivating cells. During the experiments the cells were pre-incubated in hypoxic conditions and the experiment and recovery period also subject to the same oxygenic conditions. Although it has been demonstrated that the dominant effect of oxygen on radiosensitivity requires it present during or within msecs of irradiation, however the overall response is likely to be modulated to some degree by the presence or absence of oxygen effecting the response of a cell to the radiation induced damage and background levels of damage caused by oxidative stress. Post-irradiation hypoxia has been shown to eliminate potentially lethal damage recovery (PLDR) in cells irradiated under hypoxia. However, when returned to euoxic conditions the inhibition of PLDR by hypoxia was relieved.

Here it was shown that irradiation did not result in any significant reduction in cell numbers in cells incubated with either of the titania nanoparticle controls. However, the gadolinium doped titania nanoparticles still showed a significant increase in cell death upon irradiation. This indicates that the doped titania nanoparticles would be effective as radiosensitizers even under the hypoxic conditions seen in tumour cells.

Synthesis of Composite Embolization Particle

To add to the utility of the doped titania nanoparticles, a composite embolization microparticle was prepared in which the surface of bland embolic polystyrene microparticles were coated with the radiosensitizer nanoparticles. To achieve good coverage of the microparticles, a number of methods were attempted for the attachment of the nanoparticles. The first method was a one-pot method which used methacryloxypropyl trimethoxysilane (MS) to anchor the titania onto the surface of the polystyrene spheres during the course of the microparticle polymerization reaction. However, during the synthesis reaction it was found that the MS coating inhibited the UV photoactivity of the titania radiosensitizer nanoparticles, and by extrapolation the ability to generate ROS by X-ray excitation. A second method used the positively charged polyelectrolyte PDADMAC to electrostatically bind the titania nanoparticles onto the surface of pre-prepared polystyrene spheres. A reasonable coverage could be attained but there was concern that the titania nanoparticles could detach from the polystyrene spheres and be released within the body. In the context of our nanoparticles, enzymes in the blood stream could potentially cause the degradation of the PDADMAC electrolyte and release the titania nanoparticles from the surface of embolic particles.

The final and most successful method for producing the PS-titania particles made use of a sintering method. Pre-prepared polystyrene spheres were suspended in a bath of titania and then heated to ≥165° C.; the glass transition temperature of the polystyrene spheres. Sintering the polystyrene titania mixture at 165° C. resulted in approximately 70% microparticle coverage with the titania nanoparticle, while increasing the sintering temperature to both 200° C. and 230° C. increased the coverage to almost 100%. It was important to keep the sintering temperature below 260° C., at which point the polystyrene starts to degrade as indicated by a decrease in the mass. It was also desirable to keep the firing time and temperature to a minimum since the crystal structure of the titania nanoparticles may be adversely affected. (As a control, unbound nanoparticles were treated to the same sintering procedure, and it was shown that there was no significant difference ($p \geq 0.05$) in activity before and after sintering.) The ability of the doped titania nanoparticles and PS-titania embolic particles to inhibit cell proliferation was tested in vitro on the RD cell line. There was a very significant decrease of 56.9%±11.4 ($p \leq 0.005$) in the number of live cells for cells treated with the $TiO_2$:5% Gd radiosensitizer nanoparticles, compared to control cells (which were not incubated with nanoparticles) but received the same dose of irradiation. There was also a very significant difference in the number of surviving cells between cells incubated with the $TiO_2$:5% Gd radiosensitizer and either unirradiated or irradiated with 3Gy.

This is the first time that a radiosensitising embolic particle has been demonstrated which is inert without radiation but which can be activated using X-rays to enhance cell kill. The radiosensitizer embolization particles shown herein are a proof-of-concept and may be further modified for greater utility. The range of sizes of tumour vessels and the size of the bland embolization particle may be altered with ease to provide the maximal size for occlusion of the vessel. Furthermore multimodal embolization particles may be created by the addition of fluorescent markers or MRI contrast agents in to the centre of the microparticles in addition to the modification of the surface to generate a radiosensitizer. The microparticles can also incorporate imaging agents such as fluorophores or heavy metals such as tantalum as X-ray contrast agents (non-magnetic so allows patient to undergo MRI), or combination with chemoembolization (a mixture of mesoporous silica nanoparticles and titania nanoparticles).

The invention claimed is:

1. An embolization particle comprising a microparticle coated with a plurality of nanoparticles, which nanoparticles comprise a metal oxide doped with one or more rare earth elements, wherein the metal oxide is titanium dioxide, zinc oxide or cerium dioxide.

2. An embolization particle according to claim 1, wherein the metal oxide is titanium dioxide.

3. An embolization particle according to claim 1, wherein the one or more rare earth elements are selected from Sc, Y, La, Ce, Pr, Nd, Pm, Sm, Eu, Gd, Tb, Dy, Ho, Er, Tm and Yb.

4. An embolization particle according to claim 1, wherein the metal oxide is doped with the one or more rare earth elements in a total amount of from 0.1 to 25 mol % relative to the amount of metal oxide.

5. An embolization particle according to claim 1, wherein the nanoparticles have an average diameter of less than 200 nm.

6. An embolization particle according to claim 1, wherein the microparticle has a diameter of from 1 to 500 μm or of from 10 to 200 μm.

7. An embolization particle according to claim 1, wherein the microparticle comprises one or more materials selected from a polymer, a metal and an inorganic compound.

8. An embolization particle according to claim 7, wherein the microparticle comprises one or more polymers or copolymers selected from polyalkenes, polyacrylates, polyesters and polyether, preferably wherein the polymer or copolymer is cross-linked.

9. An embolization particle according to claim 8, wherein the microparticle comprises a polymer or copolymer formed from styrene monomer units.

10. An embolization particle according to claim 1, wherein the embolization particle further comprises a plurality of radioopaque nanoparticles.

11. An embolization particle according to claim 10, wherein the radioopaque nanoparticles are incorporated into the microparticle.

12. An embolization particle according to claim 10, wherein the radioopaque nanoparticles comprise tantalum oxide, gold, or bismuth (III) sulfide.

13. An embolization particle according to claim 1, wherein the embolization particle further comprises a chemotherapeutic agent.

14. An embolization particle according to claim 13, wherein the embolization particle further comprises a plurality of nanoparticles which comprise the chemotherapeutic agent.

15. An embolization particle according to claim 14, wherein:
the nanoparticles which comprise the chemotherapeutic agent are coated onto the surface of the microparticle; and/or
the nanoparticles which comprise the chemotherapeutic agent are silica nanoparticles.

16. A composition comprising a plurality of embolization particles, wherein each embolization particle comprises a microparticle coated with a plurality of nanoparticles, which nanoparticles comprise a metal oxide doped with one or more rare earth elements, wherein the metal oxide is titanium dioxide, zinc oxide or cerium dioxide.

17. A composition according to claim 16, wherein the embolization particles have an average diameter of from 10 to 200 μm.

18. A pharmaceutical composition comprising: a plurality of embolization particles, wherein each embolization particle comprises a microparticle coated with a plurality of nanoparticles, which nanoparticles comprise a metal oxide doped with one or more rare earth elements, wherein the metal oxide is titanium dioxide, zinc oxide or cerium dioxide; and one or more pharmaceutically acceptable excipients or diluents.

* * * * *

SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: nuclear localization signal (NLS) peptide

```
<400> SEQUENCE: 1

Pro Pro Lys Lys Lys Arg Lys Val
1               5

<210> SEQ ID NO 2
<211> LENGTH: 13
<212> TYPE: PRT
<213> ORGANISM: Artificial Sequence
<220> FEATURE:
<223> OTHER INFORMATION: nuclear localization signal (NLS) peptide

<400> SEQUENCE: 2

Cys Gly Gly Phe Ser Thr Ser Leu Arg Ala Arg Lys Ala
1               5                   10
```